(12) United States Patent
Imbert et al.

(10) Patent No.: US 7,456,192 B2
(45) Date of Patent: Nov. 25, 2008

(54) 3β-AMINO AZABICYCLOOCTANE HETEROAROMATIC AMID DERIVATIVES PREPARATION METHOD AND THERAPEUTIC USES THEREOF

(75) Inventors: Thierry Imbert, Viviers les Montagnes (FR); Barbara Monse, Weichs (DE); Wouter Koek, San Antonio, CA (US)

(73) Assignee: Pierre Fabre Medicament, Boulogne Billancourt (FR)

( * ) Notice: Subject to any disclaimer, the term of this patent is extended or adjusted under 35 U.S.C. 154(b) by 362 days.

(21) Appl. No.: 10/494,639

(22) PCT Filed: Oct. 30, 2002

(86) PCT No.: PCT/FR02/03737

§ 371 (c)(1),
(2), (4) Date: Dec. 2, 2004

(87) PCT Pub. No.: WO03/037904

PCT Pub. Date: May 8, 2003

(65) Prior Publication Data

US 2005/0080085 A1    Apr. 14, 2005

(30) Foreign Application Priority Data

Nov. 2, 2001  (FR) .................... 01 14220

(51) Int. Cl.
| | |
|---|---|
| A61K 31/4353 | (2006.01) |
| A61K 31/4365 | (2006.01) |
| A61K 31/46 | (2006.01) |
| C07D 471/04 | (2006.01) |
| C07D 419/04 | (2006.01) |

(52) U.S. Cl. ............. 514/279; 514/301; 514/302; 514/304; 544/350; 546/114; 546/115

(58) Field of Classification Search ............ 546/114, 546/115; 544/350; 514/304, 249, 301, 302
See application file for complete search history.

(56) References Cited

U.S. PATENT DOCUMENTS

| 4,536,580 A | 8/1985 | Dostert et al. |
|---|---|---|
| 4,910,193 A | 3/1990 | Buchheit |

FOREIGN PATENT DOCUMENTS

| EP | 0013138 | 12/1979 |
|---|---|---|
| WO | WO 93/15052 | 8/1993 |
| WO | WO 97/10244 | 3/1997 |
| WO | WO 01/14333 | 3/2001 |

OTHER PUBLICATIONS

Dorwald F. A. Side Reactions in Organic Synthesis, 2005, Wiley: VCH, Weinheim p. IX of Preface.*
"Antipsychotic Drugs, Neurotransmitters, and Schizophrenia" Carlsson A., Am.J. Psychiatry, 135, 164-173, 1978.
"New drugs for the treatment of schizophrenic patients" Acta Psychiatr. Scand., 1995, 91 (Suppl 388): 24-30.
Dopamine D2 receptors selectively labeled by a benazmide neuroleptic . . . : H.B. Niznik et al, Naunyn-Schmiedeberg's Arch. Pharmacol. 329-333-343, 1985.
"Inhibition of Methylphenidate-Induced Behaviors in Rats: Differences Among Neuropleptics", W. Koek, F.C. Colpaert, J. Pharmacol. Exp. Ther. 267, 181-191, 1993.
"Tropapride hydrochloride", Drugs of the Future, vol. 9, No. 9, 673-674, 1984.
"The cataleptogenic effects of the neuroleptic nemonapride are attenuated by its 5-HT receptor agonist properties", e. Prinssen et al, Eur. J. Pharmacol. 356, 189-192, 1998.
"Studies on the neuroleptic benzamides III-Synthesis and antidopaminergic properties of new 3-nortropane deriatives", Sostert et al, Eur. J. Med. Chem. 1984, 19, 105-110.
M.N. Romanelli, et al. "Synthesis and Biological Activity of a Series of Aryl Tropanyl Esters and Amides Chemically Related to 1H-Indole-3-carboxylic Acid endo 8-Methyl-8-azabicyclo[3.2.1]oct-3-yl Ester", Arzneim.-Forsch. (1993), pp. 913-918.

* cited by examiner

*Primary Examiner*—Rita J Desai
(74) *Attorney, Agent, or Firm*—Birch, Stewart, Kolasch & Birch, LLP

(57) ABSTRACT

The invention concerns compounds of general formula 1, wherein: A, B, D and E represent one or two nitrogen atoms, the others being carbon atoms; X represents a S or, a O, thereby forming a bicyclic fused heteroaromatic, such as thieno[2,3-b]pyridine, furo[2,3-b]pyridine, thieno[3,2-b]pyridine, furo[3,2-b]pyridine, thieno[2,3-b]pyrazine, furo[2,3-b]pyrazine, thieno[2,3-c]pyridine, furo[2,3-c]pyridine, thieno[3,2-c]pyridine and furo[3,2-c]pyridine; R1 represents a linear or branched $C_1$-$C_6$ alkoxy group, a linear or branched $C_1$-$C_6$ alkylthio group; R2 represents a linear, branched, cyclic $C_2$-$C_8$ group, a 2- or 3-thienylmethyl group, or a benzyl group optionally substituted by one or several halogens, F, Cl, Br, I, $C_1$-$C_4$alkyl, $C_1$-$C_4$ alkoxy, CF3, CN, NO2, OH; and their pharmaceutically acceptable salts. Said compounds are anti-dopaminergic agents.

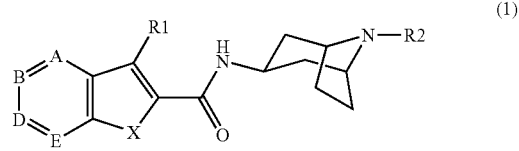

(1)

10 Claims, No Drawings

3β-AMINO AZABICYCLOOCTANE HETEROAROMATIC AMID DERIVATIVES PREPARATION METHOD AND THERAPEUTIC USES THEREOF

The present patent application is a non-provisional application of International Application No. PCT/FR02/03737, filed Oct. 30, 2002.

The present invention relates to new 3-heteroaroyl amino-N-benzyl-8-aza-bicyclo(3.2.1)octane derivatives, the preparation method and use thereof as a medicinal product.

These compounds are antidopaminergic agents, and thus used as antipsychotic medicinal products to treat schizophrenia or central nervous system disorders sensitive to antidopaminergic treatment, such as, for example, obsessive-compulsive disorders, anxiety, depression, autism, late dyskinesia, drug addiction and gastrointestinal disorders.

The need for an antidopaminergic activity, particularly on subclass D2 receptors, represents a conventional approach to the treatment of schizophrenia (Carlsson A., Am. J. Psychiatry, 135, 164, 1978). However, the majority of the compounds with such a mode of action have the drawback of showing, in clinical practice, adverse side effects, particularly extrapyramidal effects (see Acta Psychiatr. Scand. 1995, 91 (Suppl 388): 24-30).

The 3β-amino tropane group has been used in the benzamide series to obtain compounds with a high antidopaminergic activity (EP 13138, U.S. Pat. No. 4,536,580). These products show varying degrees of antipsychotic activity, defined in these publications, but are not, however, free from cataleptic side effects and therefore cannot be used in clinical practice. Amino-3β-nortropane amides have been patented, for example WO 93/15052 describes calcium channel antagonist compounds. The U.S. Pat. No. 4,910,193 describes esters or amides for the treatment of serotonin-induced gastrointestinal disorders. The patent WO 01/14333 describes eosinophilic chemotaxis modulating compounds. None describes the use of compounds according to the general formula for the treatment of schizophrenia. The closest priority consists of our previous patent (FR 95/10655) describing 3β-amino azabicyclo(3,2,1)octane naphthamide products. These products are powerful dopaminergic and serotininergic antagonists. The products of the present invention are characterized in that they are much less cataleptic and thus show a better activity profile.

It was found that merged heteroaromatic amide 3-heteroaroyl amino-N-benzyl-8-aza-bicyclo(3.2.1)octane derivatives show a powerful antipsychotic activity, as can be demonstrated on the methylphenidate-induced behavior inhibition test on rats, with no adverse side effects, and are also free from cataleptic effects (extrapyramidal syndromes).

The present invention relates to new 3-heteroaroyl amino-N-benzyl-8-aza-bicyclo(3.2.1)octane derivatives, the preparation method thereof, their pharmaceutically acceptable salt form, pharmaceutical formulations containing same and the application thereof as a medicinal product for human therapeutic use, particularly as antipsychotics.

These new compounds comply with formula 1

Formula 1

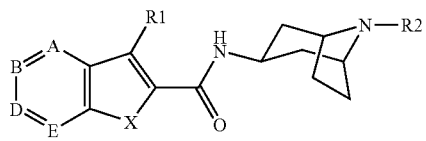

wherein A, B, D and E represent one or two nitrogen atoms, the others being carbon atoms.

X represents an S, or an O, thus forming a bicyclic merged heteroaromatic system such as thieno-pyridine, thieno-pyrazine, furo-pyridine, furo-pyrazine.

R1 represents a linear or branched C1-C6 alcoxy group, a linear or branched C1-C6 thio alkyl group.

R2 represents a C2-C8 linear, branched, cyclic alkyl group, a thiophen-2 or 3-ylmethyl group, i.e. a benzyl group possibly substituted by one or more substituents such as halogens, F, Cl, Br, I, C1-4 alkyl, C1-C4 alcoxy, CF3, CN, NO2, OH.

Preferentially, the heteroaromatic group forms a thieno[2,3-b]pyridine network, furo[2,3-b]pyridine, thieno[3,2-b]pyridine, furo[3,2-b]pyridine, thieno[2,3-b]pyrazine, furo[2,3-b]pyrazine, the R1 group is a methoxy or ethoxy, the R2 group is a cyclohexylmethyl, a thiophen-2 or 3-ylmethyl, or a non-substituted benzyl, or substituted by one or more F, Cl, OCH3, CN, and corresponding to the following compounds:

3-Methoxythieno[2,3-b]pyridine-2-carboxylic acid (8-benzyl-8-azabicyclo[3.2.1]oct-3β-yl)amide 3-Methoxythieno[3,2-b]pyridine-2-carboxylic acid (8-benzyl-8-azabicyclo[3.2.1]oct-3β-yl)amide 3-Methoxyfuro[3,2-b]pyridine-2-carboxylic acid (8-benzyl-8-azabicyclo[3.2.1]oct-3β-yl)amide 3-Methoxythieno[3,2-c]pyridine-2-carboxylic acid (8-benzyl-8-azabicyclo[3.2.1]oct-3β-yl)amide 3-Methoxythieno[2,3-b]pyridine-2-carboxylic acid [8-(4-chlorobenzyl)-8-azabicyclo[3.2.1]oct-3β-yl]amide 3-Methoxythieno[2,3-b]pyridine-2-carboxylic acid [8-(4-methoxybenzyl)-8-azabicyclo[3.2.1]oct-3β-yl]amide 3-Methoxythieno[2,3-b]pyridine-2-carboxylic acid [8-(cyclohexylmethyl-8-azabicyclo[3.2.1]oct-3β-yl]amide 3-Methoxythieno[2,3-b]pyridine-2-carboxylic acid [8-(4-fluorobenzyl)-8-azabicyclo[3.2.1]oct-3β-yl]amide 3-Methoxythieno[2,3-b]pyridine-2-carboxylic acid [8-thiophen-3-ylmethyl-8-azabicyclo[3.2.1]oct-3β-yl]amide 3-Methoxythieno[2,3-c]pyridine-2-carboxylic acid (8-benzyl-8-azabicyclo[3.2.1]oct-3β-yl)amide 3-Isopropoxythieno[2,3-b]pyridine-2-carboxylic acid (8-benzyl-8-azabicyclo[3.2.1]oct-3β-yl)amide 3-Ethoxythieno[2,3-b]pyridine-2-carboxylic acid (8-benzyl-8-azabicyclo[3.2.1]oct-3β-yl)amide 3-Methoxyfuro[3,2-b]pyridine-2-carboxylic acid [8-(4-fluorobenzyl)-8-azabicyclo[3.2.1]oct-3β-yl]amide 3-Methoxyfuro[3,2-b]pyridine-2-carboxylic acid [8-(4-chlororobenzyl)-8-azabicyclo[3.2.1]oct-3β-yl]amide 3-Methoxyfuro[3,2-b]pyridine-2-carboxylic acid (8-cyclohexylmethyl-8-azabicyclo[3.2.1]oct-3β-yl)amide 3-Methylsulfanylthieno[2,3-b]pyridine-2-carboxylic acid (8-benzyl-8-azabicyclo[3.2.1]oct-3β-yl)amide 3-Methoxythieno[2,3-b]pyrazine-2-carboxylic acid (8-benzyl-8-azabicyclo[3.2.1]oct-3β-yl)amide 3-Methoxythieno[2,3-b]pyrazine-2-carboxylic acid [8-(4-chlorobenzyl)-8-azabicyclo[3.2.1]oct-3β-yl]amide 3-Methylsulfanylthieno[2,3-b]pyrazine-2-carboxylic acid (8-benzyl-8-azabicyclo[3.2.1]oct-3β-yl)amide 3-Methylsulfanylthieno[2,3-b]pyrazine-2-carboxylic acid [8-(4-chlorobenzyl)-8-azabicyclo[3.2.1]oct-3β-yl]amide 3-Methoxythieno[2,3-b]pyrazine-2-carboxylic acid [8-(4-fluorobenzyl)-8-azabicyclo[3.2.1]oct-3β-yl]amide 3-Methylsulfanylthieno[2,3-b]pyrazine-2-carboxylic acid [8-(4-fluorobenzyl)-8-azabicyclo[3.2.1]oct-3β-yl]amide 3-Methoxythieno[2,3-b]pyrazine-2-carboxylic acid (8-thiophen-2-ylmethyl-8-azabicyclo[3.2.1]oct-3β-yl) amide 3-Methoxyfuro[2,3-b]pyrazine-2-carboxylic acid (8-benzyl-8-azabicyclo[3.2.1]oct-3β-yl)amide 3-Methoxyfuro[2,3-b]pyrazine-2-carboxylic acid [8-(4-chlorobenzyl)-8-azabicyclo[3.2.1]oct-3β-yl]amide 3-Methoxyfuro[2,3-b]pyrazine-2-carboxylic acid [8-(4-fluorobenzyl)-8-azabicyclo[3.2.1]oct-3β-yl]amide The products of the present invention are D2 type central dopaminergic receptor ligands. Their properties are demonstrated on the basis of their affinity on dopaminergic receptors, by displacement of the radioactive ligand ($^3$H-YM-09151-2) which specifically labels these receptors. This specific bond study method is described in Naunyn-Schmiedeberg's Arch.Pharmcol. 21, 301-314, 1982.

By way of example, the values are given in Table 1 below, in comparison to reference substances.

TABLE 1

| Compounds: | Examples No. | D2 affinity (pKi) |
|---|---|---|
| Haloperidol | | 9.01 |
| Sulpiride | | 8.39 |
| Risperidone | | 8.7 |
| Spiperone | | 10 |
| Tropapride | | 10.02 |
| | 32 | 9.17 |
| | 29 | 9.18 |
| | 31 | 8.69 |
| | 27 | 9.36 |
| | 2 | 9.35 |
| | 11 | 9.11 |
| | 10 | 8.59 |
| | 12 | 8.59 |
| | 8 | 8.76 |
| | 4 | 8.69 |

The affinity values on the D2 receptors are comparable to those of the reference products. The power of this affinity is required to obtain the desired in vivo activity, measured by the normalization of methylphenidate-induced behavior, as described below.

The compounds were tested in vivo (Table II) to measure their ability to antagonize methylphenidate-induced behavior in rats. This highly discriminating test makes it possible to select compounds which prove to be active in humans as antipsychotics as demonstrated in: W. Koek, F. C. Colpaert J. Pharmacol. Exp. Ther. 267, 181 (1993). This test characterizes the antipsychotic activity in a more in-depth manner than apomorphine effect antagonism, the test conventionally used.

TABLE II

| Example No. | Chewing inhibition ED50 (mg/kg) | Normalization ED50 (mg/kg) | Catalepsy ED50 (mg/kg) * | Ratio: Catalepsy/ Normalization |
|---|---|---|---|---|
| 2 | 0.08[a] | 0.56[a] | 1.8[a] | 3.2 |
| 8 | 0.10[a] | 1.3[a] | >40[a] | >30 |
| 10 | 1.25[a] | 5[a] | >40[a] | >8 |
| 11 | 0.08[a] | 0.31[a] | >40[a] | >129 |
| 12 | 1.25[a] | 1.25[a] | >40[a] | >32 |
| 4 | 0.12[a] | 0.98[a] | >40[a] | >40 |
| 32 | 0.08[b] | 0.31[b] | 1.25[b] | 4 |
| 29 | 0.08[b] | 0.32[b] | 5[b] | 15.6 |
| 31 | 0.31[b] | 0.31[b] | 1.25[b] | 4 |
| 27 | 0.27[b] | 0.67[b] | 9.5[b] | 14 |
| Risperidone | 0.25[a] | 2.8[a] | 1.2[a] | 0.4 |
| Tropapride | 0.0059[a] | 0.017[a] | 0.015[a] | 0.9 |
| Haloperidol | 0.08[a] | 0.32[a] | 0.32[a] | 1 |
| Sulpiride | >40[a] | >40[a] | >160[a] | |

Results on an experiment on 3 or 5 animals.
[a]i.p.
[b]p.o.

Tropapride is compared as the reference product due to its tropane chemical structure (Drugs of the Future vol 9, No. 9, 673, 1984).

The results obtained demonstrate that the compounds of the invention are capable not only of inhibiting stereotypical chewing but also of normalizing all methylphenicate-induced behavior, in the absence of adverse side effects.

In addition, the compounds of the present invention are evaluated for their cataleptic activity according to the protocol described in: Eur. J. Pharmacol. 356, 189 (1998). Table II demonstrates that the reference products show a cataleptic activity at the doses at which they normalize methylphenidate-induced behavior.

The compounds of the present invention, on the other hand, show little or no catalepsy when they are evaluated alone in rats in the absence of methylphenidate. Some compounds, unlike the reference products, show a difference between the cataleptic dose and the dose inducing normalization, and in addition, others show no catalepsy at the doses studied, as indicated by the catalepsy/normalization ratio (Table II). In this way, the products of the present invention are extremely favorably positioned with respect to the reference compounds.

It has emerged from our study, and it is the subject of the invention, that the products described here have a high antipsychotic activity, without inducing adverse side effects or catalepsy at the doses used. This indicates a low tendency of these products to induce in humans the adverse extrapyramidal effects observed with numerous conventionally used products. These in vivo biological parameters represent the characteristics of the products of the invention which are distinguished from those conventionally used, and thus make it possible to solve the medical problem of the treatment of schizophrenia. The patient's comfort is thus increased during treatment, and the use of these products for the treatment of psychotic disorders by clinicians is much improved with respect to standard products, and the therapeutic margin is also improved.

Therefore, the present invention relates to compounds of general formula 1 as medicinal products particularly useful in the treatment of schizophrenia.

The compounds of the present invention may form salts by adding pharmaceutically acceptable mineral or organic acid and be used in pharmaceutical formulations to be able to be administered via the various standard routes, oral, injectable, parenteral forms.

The present invention also relates to the use of these compounds of formula 1 used in a pharmaceutical formulation formulated according to its mode of administration, tablets, capsules, suitable for human clinical practice and at daily doses between 0.1 and 500 mg or more specifically 0.1 to 100 mg of active ingredient.

The products of the present invention are obtained by analogy with known methods wherein the key step is the formation of the amide function between the heteroaromatic acid of formula 2 and the amine of formula 3, according to diagram I:

Diagram I

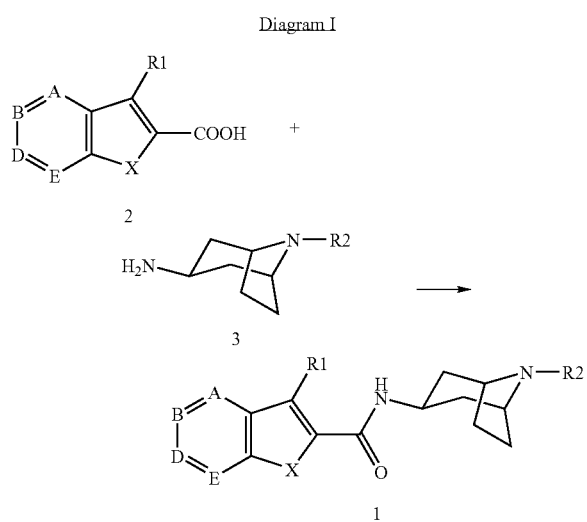

The amide bond is formed by activating the acid 2 (i.e. mixed anhydride, acid chloride) with an amine 3 in an inert solvent (dichloromethane, THF) in the presence of a base (i.e. an amine such as pyridine or triethylamine) from 0° C. to 100° C., preferentially 0° C.

The coupling conditions involve the action of alkyl chloroformiate in the presence of triethylamine, in methylene chloride, at a low temperature or the action of the acid chloride of the corresponding heterocyclic acid.

Access to the heterocyclic acid systems 2 is described in the chemical literature.

3-hydroxy-2-methoxycarbonylthieno[3,2-b]pyridine, 3-hydroxy-2-methoxycarbonylthieno[2,3-b]pyridine, 3-hydroxy-2-methoxycarbonylthieno[3,2-c]pyridine, 3-hydroxy-2-methoxycarbonylthieno[2,3-c]pyridine are described in Journal of Heterocyclic Chemistry 1987, 24, 85. 3-hydroxy-2-ethoxycarbonylfuro[2,3-c]pyridine is described in Journal of Heterocyclic Chemistry, 1986, 23, 549. 3-hydroxy-2-ethoxycarbonylfuro[3,2-b]pyridine is described in Journal of Heterocyclic Chemistry, 1986, 23, 665. 3-hydroxy-2-ethoxycarbonylfuro[2,3-b]pyridine is described in Journal of Heterocyclic Chemistry, 1986, 23, 1465. 3-hydroxy-2-ethoxycarbonylfuro[3,2-c]pyridine is described in Journal of Heterocyclic Chemistry, 1988, 25, 1205.

The above heterocyclic products comprising a 3-hydroxy function may be alkylated under conventional conditions, such as dimethyl sulfate or an alkyl iodide, in acetonitrile or acetone in the presence of potassium carbonate. The saponification of the ester function in position 2 by KOH or NaOH in an alcohol supplies the type 2 acids.

The compounds comprising a methylthio group in position 3 are obtained by substituting a starting group, such as a phosphate in position 3 of the heterocyclic system, by a thiol such as an alkyl mercaptan, in an inert solvent. This method is described in the patent WO 9313664.

3-hydroxy-2-methoxycarbonylthieno[2,3-b]pyrazine is obtained from 2-chloro-3-methoxycarbonylpyrazine, in turn described in Journal of the Chemical Society 1996, 247-254. The chlorine in position 2 of this pyrazine is substituted by methyl thioglycolate in a basic medium, and the adduct obtained is aromatized in the same reaction into 3-hydroxy-2-methoxycarbonylthieno[2,3-b]pyrazine. 3-hydroxy-2-methoxycarbonylfuro[2,3-b]pyrazine is obtained with the same transformation using methyl glycolate.

The diamine of formula 3 (Diagram I) is described in Eur. J. Med. Chem. 1984, 19, 105. It comprises a substituent R2, which may be a substituted benzyl group. Debenzylation by means of hydrogenolysis on palladium-plated charcoal requires prior protection of the primary amine with a carbamate type protective group such as terbutoxycarbonyl, that can subsequently be split in an acid medium. The alkylation of the secondary amine from the hydrogenolysis, the primary amine being protected, is performed by conventional and unequivocal means with different substituted benzyl halides. Better yields are obtained by means of reflux alkylation in methylethyl ketone, in the presence of cesium carbonate, and the addition of traces of potassium iodide. It is also possible to perform debenzylation on the compound of general formula 1 when R2 is a benzyl group, with ammonium formiate in the presence of palladium hydroxide on charcoal, in a hydroalcoholic medium. The amines 3 may also be obtained by reducing amination of aromatic aldehydes such as 2-thiophencarboxaldehyde, with ter-butyl-N-(8-azabicyclo [3.2.1]oct-3β-yl)carbamate, with sodium triacetoxyborohydride in acetic acid.

The present invention also relates to compounds of formula 4, as synthesis intermediates, wherein X is an O or S, R1 an OH, a C1-6 alcoxy, or a C1-6 thioalcoxy, and R represents a hydrogen, except when R1 is OH, a methyl or an ethyl.

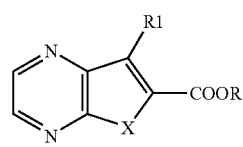

The preferred compounds of formula 4 are selected from:
3-hydroxy-2-methoxycarbonylfuro[2,3-b]pyrazine
3-methylsulfanyl-2-methoxycarbonylfuro[2,3-b]pyrazine
3-methoxy-furo[2,3-b]pyrazine-2-carboxylic acid
3-ethoxy-furo[2,3-b]pyrazine-2-carboxylic acid
3-methylsulfanylfuro[2,3-b]pyrazine-2-carboxylic acid
3-hydroxy-2-methoxycarbonylthieno[2,3-b]pyrazine
3-methylsulfanyl-2-methoxycarbonylthieno[2,3-b]pyrazine
3-methoxythieno[2,3-b]pyrazine-2-carboxylic acid
3-ethoxythieno[2,3-b]pyrazine-2-carboxylic acid
3-methylsulfanylthieno[2,3-b]pyrazine-2-carboxylic acid These products are prepared by means of the action of glycolic acid esters on 3-chloro-2-pyrazine methyl carboxylate, in a basic medium.

The following examples illustrate the invention:

EXAMPLE 1

3-Methoxythieno[2,3-b]pyridine-2-carboxylic acid (8-benzyl-8-azabicyclo[3.2.1]oct-3β-yl)amide hydrochloride a) 3-Methoxy-2-methoxycarbonylthieno[2,3-b]pyridine 995 mg of 3-hydroxy-2-methoxycarbonylthieno[2,3-b]pyridine (4.76 mmol, 1 eg.) is reflux heated for 4 hrs with 0.54 ml of dimethyl sulfate (5.71 mmol, 1.2 eq.) in 30 ml of acetone in the presence of 987 mg of potassium carbonate (7.14 mmol, 1.5 eq.). The insoluble is filtered, washed with acetone and vacuum evaporated.

600 mg of product (56%) is obtained after rapid filtration on silica.

NMR ($^1$H, CDCl$_3$): 3.90 (s; 3H, OCH$_3$), 4.15 (s; 3H, OCH$_3$), 7.31 (dd, J=8.3, 4.7 Hz; 1H), 8.12 (dd, J=8.3, 1.5 Hz; 1H), 8.67 (dd, J=4.7, 1.5 Hz; 1H).

b) 3-Methoxythieno[2,3-b]pyridine-2-carboxylic acid 590 mg of 3-methoxy-2-methoxycarbonylthieno[2,3-b]pyridine (2.64 mmol, 1 eq.) obtained above in step a) is reflux heated for 1 hr with 4.0 ml of NaOH (4.0 mmol, 1.5 eq.) in 10 ml of ethanol. It is allowed to return to ambient temperature, diluted with water and neutralized with 4.5 ml of 1N HCl. The precipitate formed is filtered, washed with water and dried.

500 mg of product (91%) is obtained.

NMR ($^1$H, DMSO-d$_6$): 4.10 (s; 3H, OCH$_3$), 7.53 (dd, J=8.1, 4.5 Hz; 1H), 8.30 (dd, J=8.1, 1.4 Hz; 1H), 8.74 (dd, J=8.1, 1.4 Hz; 1H), 13.55 (large; 1H, COOH).

c) 3-Methoxythieno[2,3-b]pyridine-2-carboxylic acid (8-benzyl-8-azabicyclo[3.2.1]oct-3β-yl)amide hydrochloride 0.25 ml of ethyl chloroformiate (2.6 mmol, 1 eq.) in 50 ml of dichloromethane is added to a solution of 496 mg of 3-methoxythieno[2,3-b]pyridine-2-carboxylic acid (2.4 mmol, 1 eq.) obtained in step b) above, in 100 ml of dichloromethane at 0° C. in the presence of 0.4 ml of triethylamine (2.8 mmol, 1.2 eq.). After 15 min, a solution of 487 mg of 8-(phenylmethyl)-8-azabicyclo[3.2.1]octane-3β-amine (2.25 mmol, 0.95 eq.) in 50 ml of dichloromethane is introduced drop by drop. Stirring is then carried out at ambient temperature until the starting products have all been used up. The solution obtained is washed three times with water, dried and the solvent is evaporated.

455 mg of product (47%) is obtained after flash chromatography on silica and chromatography on alumina.

Salt preparation:

455 mg of the base (1.1 mmol, 1 eq.) obtained is dissolved in 5 ml of ethanol. 0.6 ml of an isopropanol—3.6N HCl solution (2.2 mmol, 2 eq.) is introduced. The solution is vacuum evaporated, taken up with ethyl acetate, the salt formed is filtered and dried.

Yield: 368 mg (85%).

FP=228° C.

IR: 3355, 1645, 1540

NMR (base; $^1$H, CDCl$_3$): 1.65 (m; 2H), 1.78 (m; 2H), 1.95 (m; 2H), 2.09 (m; 2H), 3.29 (m; 2H, H1 and H5), 3.55 (s; 2H, N—CH$_2$-Ph), 4.27 (s; 3H, OCH$_3$), 4.40 (m; 1H, H3), 7.26 (m; 2H), 7.35 (m; 3H), 7.39 (m; 2H), 8.08 (dd, J=8.1, 1.3 Hz; 1H), 8.65 (dd, J=4.5, 1.3 Hz; 1H)

| Analysis: | C$_{23}$H$_{25}$N$_3$O$_2$S | Mass = 407.54 |
|---|---|---|
| | C$_{23}$H$_{25}$N$_3$O$_2$S, HCl | Mass = 444.00 |
| | C$_{23}$H$_{25}$N$_3$O$_2$S, HCl, 0.1 H$_2$O | Mass = 445.80 |

| | % C | % H | % N | % H$_2$O |
|---|---|---|---|---|
| calc. | 61.97 | 5.92 | 9.43 | 0.4 |
| detect. | 61.98 | 5.95 | 9.47 | 0.3 |

EXAMPLE 2

3-Methylsulfanylthieno[2,3-b]pyridine-2-carboxylic acid (8-benzyl-8-azabicyclo[3.2.1]oct-3β-yl)amide hydrochloride a) 3-(Diethoxyphosphoryloxy)thieno[2,3-b]pyridine-2-carboxylic acid methyl ester 261 mg of NaH (60% in mineral oil; 6.54 mmol, 1.2 eq.) is added to a suspension of 1.14 g of 3-hydroxy-2-methoxycarbonylthieno[2,3-b]pyridine (5.45 mmol, 1 eq.) (obtained as per J. Heteroc. Chem. 1987, 24, 85) in 20 ml of tetrahydrofuran at 0° C. in nitrogen. The reaction mixture is then left under stirring at ambient temperature for 18 hrs. The reaction medium is poured onto 100 ml of chilled water, acidified with 1N HCl and extracted 3 times with ethyl acetate. The organic phase is dried on Na$_2$SO$_4$ and vacuum evaporated. 750 mg (40%) of purified product is obtained with flash chromatography on silica (eluent: ethyl acetate/petroleum ether=2/3).

NMR ($^1$H, CDCl$_3$): 1.37 (t, J=7.2 Hz; 6H), 3.95 (s; 3H), 4.32 (q, J=7.2 Hz; 4H), 7.39 (dd, J=8.2, 4.6 Hz; 1H), 8.42 (dd, J=8.2, 1.6 Hz; 1H), 8.71 (dd, J=4.6, 1.6 Hz; 1H)

b) 3-Methylsulfanylthieno[2,3-b]pyridine-2-carboxylic acid methyl ester

A solution of 736 mg of the product from step a) above (2.13 mmol, 1 eq.) in 15 ml of tetrahydrofuran is added to a suspension of 300 mg of sodium thiomethoxide (4.26 mmol, 2 eq.) in 5 ml of tetrahydrofuran at 0° in nitrogen. The reaction medium is then left at ambient temperature for 5 days. 10 ml of water is added, the solution is acidified with 1N HCl and extracted 3 times with ethyl acetate. The organic phase is dried on Na$_2$SO$_4$ and vacuum evaporated.

270 mg (55%) of product is obtained after flash chromatography on silica (eluent: ethyl acetate/petroleum ether=1/9).

NMR ($^1$H, CDCl$_3$): 2.50 (s; 3H), 3.86 (s; 3H), 7.52 (dd, J=8.1, 4.6 Hz; 1H), 8.36 (dd, J=8.1, 1.6 Hz; 1H), 8.74 (dd, J=4.6, 1.7 Hz; 1H).

c) 3-Methylsulfanylthieno[2,3-b]pyridine-2-carboxylic acid 270 mg of product from step b) above (1.1 mmol, 1 eq.) is reflux heated for 18 hrs in 20 ml of a 50/50 H$_2$O/methanol mixture in the presence of 1.7 ml of 1N NaOH (1.7 mmol, 1.5 eq.). The solution is allowed to return to ambient temperature, water is added and 2 ml of 1N HCl is added. The precipitate formed is filtered, washed with water and dried.

242 mg of acid (95%) is obtained.

FP=214° C.

NMR ($^1$H, DMSO-d$_6$): 2.51 (s; 3H), 7.60 (dd, J=8.1, 4.5 Hz; 1H), 8.46 (dd, J=8.1, 1.5 Hz; 1H), 8.77 (dd, J=4.5, 1.5 Hz; 1H), 13.92 (s; large, 1H)

d) 3-Methylsulfanylthieno[2,3-b]pyridine-2-carboxylic acid (8-benzyl-8-azabicyclo[3.2.1]oct-3β-yl)amide hydrochloride This compound is obtained according to the same method as for example 1c).

FP=236° C.

IR=1637, 1534

NMR (base; $^1$H, CDCl$_3$): 1.72 (m; 2H), 1.78 (m; 2H), 1.98 (m; 2H), 2.10 (m; 2H), 2.41 (s; 3H, SCH$_3$), 3.31 (m; 2H, H1 and H5), 3.57 (s; 2H, N—CH$_2$-Ph), 4.43 (m; 1H, H3), 7.26 (m; 2H), 7.34 (t, J=7.2 Hz; 2H), 7.41 (m; 3H), 8.26 (dd, J=8.2, 1.6 Hz; 1H), 8.58 (dd, J=8.0 Hz, 1H, NH), 8.68 (dd, J=4.6, 1.6 Hz; 1H)

| Analysis: | C$_{23}$H$_{25}$N$_3$OS$_2$ | Mass = 423.60 |
|---|---|---|
| | C$_{23}$H$_{25}$N$_3$OS$_2$, 2 HCl | Mass = 496.52 |
| | C$_{23}$H$_{25}$N$_3$OS$_2$, 2 HCl, 0.1 H$_2$O | Mass = 505.53 |

| | % C | % H | % N | % H$_2$O |
|---|---|---|---|---|
| calc. | 54.65 | 5.58 | 8.31 | 1.8 |
| detect. | 54.67 | 5.55 | 8.22 | 2.2 |

MS: M$^+$=423.9 (100%)

EXAMPLE 3

3-Methoxythieno[2,3-b]pyridine-2-carboxylic acid (8-benzyl-8-azabicyclo[3.2.1]oct-3β-yl)amide hydrochloride a) 3-Bromo-2-picoline

This compound is obtained as per the method described in J. Med. Chem. 1987, 30, 877.

NMR ($^1$H, CDCl$_3$): 2.67 (s; 3H), 7.01 (dd, J=7.9, 4.7 Hz; 1H), 7.80 (dd, J=7.9, 1.0 Hz; 1H), 8.43 (dd, J=4.7, 1.0 Hz; 1H)

b) 3-Bromo-2-pyridine carboxylic acid

This compound is obtained as per the method described in J. Med. Chem. 1974, 17, 1065.

NMR ($^1$H, DMSO-d$_6$): (5.75 (large), 7.48 (dd, J=8.1, 4.6 Hz; 1H), 8.20 (dd, J=8.1, 1.0 Hz; 1H), 8.59 (dd, J=4.6, 1.0 Hz; 1H)

c) 3-Bromo-2-pyridine carboxylic acid methyl ester

A mixture of 5.45 g of 3-bromo-2-pyridine carboxylic acid (27.0 mmol, 1 eq.), obtained in example 3b), in 100 ml of methanol is reflux heated in the presence of 8 ml of sulfuric acid. The reaction mixture is allowed to return to ambient temperature and poured into water. It is extracted 3 times with ethyl acetate, the organic phase is dried on Na$_2$SO$_4$ and vacuum evaporated. 2.48 g (42%) of esterified product is obtained.

NMR ($^1$H, CDCl$_3$): 4.02 (s; 3H), 7.34 (dd, J=8.2, 2.8 Hz; 1H), 8.04 (d, J=8.2 Hz; 1H), 8.64 (d, J=2.8 Hz; 1H).

d) 3-Hydroxythieno[3,2-b]pyridine-2-carboxylic acid methyl ester

This compound is described in J. Heterocycl. Chem. 1987, 24, 85.

A mixture of 2.48 g of the product obtained in the step in example 3c) above (11.0 mmol, 1 eq.) with 1.03 ml of methyl thioglycolate (11.0 mmol, 1 eq.) in 100 ml of acetonitrile is reflux heated in the presence of 2.4 g of potassium carbonate (17.0 mmol, 1.5 eq.). The mixture is then allowed to return to ambient temperature, the solvent is vacuum evaporated and the residue taken up with water. Acetic acid (pH 4) is added and the precipitate formed is filtered.

852 mg of product (35%) is obtained.

FP=184° C.

NMR ($^1$H, CDCl$_3$): 4.00 (s; 3H), 7.42 (dd, J=8.2, 4.4 Hz; 1H), 8.11 (dd, J=8.2, 1.3 Hz; 1H), 8.79 (dd, J=4.4, 1.3 Hz; 1H), 9.96 (large; 1H).

e) 3-Methoxythieno[3,2-b]pyridine-2-carboxylic acid methyl ester

The hydroxy is methylated according to the method in example 1a).

NMR ($^1$H, CDCl$_3$): 3.96 (s; 3H), 4.42 (s; 3H), 8.37 (dd, J=8.3, 4.4 Hz; 1H), 8.10 (dd, J=8.3, 1.3 Hz; 1H), 8.75 (dd, J=4.5, 1.3 Hz; 1H), 13.56 (large; 1H).

f) 3-Methoxythieno[3,2-b]pyridine-2-carboxylic acid (8-benzyl-8-azabicyclo[3.2.1]oct-3β-yl)amide hydrochloride This compound is obtained according to the same method as for example 1b) and 1c).

FP=239° C.

IR: 3399, 1659, 1535

NMR (base; $^1$H, CDCl$_3$): 1.68 (m; 2H), 1.78 (m; 2H), 1.96 (m; 2H), 2.09 (m; 2H), 3.29 (m; 2H, H1 and H5), 3.56 (s; 2H, N—CH$_2$-Ph), 4.38 (m; 1H, H3), 4.47 (s; 3H, OCH$_3$), 7.26-7.47 (m; 6H), 8.10 (d, J=7.2 Hz; 1H), 8.68 (d, J=3.0 Hz; 1H)

| Analysis: | C$_{23}$H$_{25}$N$_3$O$_2$S | Mass = 407.56 |
|---|---|---|
| | C$_{23}$H$_{25}$N$_3$O$_2$S, 2 HCl | Mass = 480.46 |
| | C$_{23}$H$_{25}$N$_3$O$_2$S, 2 HCl, 0.5 H$_2$O | Mass = 489.47 |

| | % C | % H | % N | % H$_2$O |
|---|---|---|---|---|
| calc. | 56.44 | 5.77 | 8.58 | 1.8 |
| detect. | 54.71 | 5.47 | 8.28 | 1.5 |

MS (DCI, NH$_3$): 408 (M$^+$, 100%).

EXAMPLE 4

3-Methoxyfuro[3,2-b]pyridine-2-carboxylic acid (8-benzyl-8-azabicyclo[3.2.1]oct-3β-yl)amide dihydrochloride a) 3-Hydroxypyridine-2-carboxylic acid ethyl ester

This compound is prepared as per Tet. Lett. 1996, 27, 459.

NMR ($^1$H, CDCl$_3$): 1.49 (t, J=7.2 Hz; 3H), 4.54 (q, J=7.2 Hz; 2H), 7.37 (dd, J=8.5, 1.4 Hz; 1H), 7.42 (dd, J=8.5, 5.4 Hz; 1H), 8.30 (dd, J=4.1, 1.4 Hz; 1H), 10.78 (s; 1H).

b) 3-Ethoxycarbonylmethoxypyridine-2-carboxylic acid ethyl ester

This compound is prepared as per J. Heterocycl. Chem. 1986, 23, 665.

NMR ($^1$H, CDCl$_3$): 1.29 (t, J=7.0 Hz; 3H), 1.44 (t, J=7.0 Hz; 3H), 4.26 (q, J=7.0 Hz; 2H), 4.47 (q, J=7.0 Hz; 2H), 4.74 (s; 2H), 7.29 (d, J=8.4 Hz; 1H), 7.39 (dd, J=8.4, 3.6 Hz; 1H), 8.35 (d, J=3.6 Hz; 1H)

c) 3-Hydroxyfuro[3,2-b]pyridine-2-carboxylic acid ethyl ester

This compound is prepared as per J. Heterocycl. Chem. 1986, 23, 665.
FP=190° C.
NMR ($^1$H, CDCl$_3$): 1.47 (t, J=7.2 Hz; 3H), 4.50 (q, J=7.2 Hz; 2H), 7.43 (dd, J=8.6, 4.6 Hz; 1H), 7.81 (d, J=8.6 Hz; 1H), 8.68 (d, J=8.6 Hz; 1H).

d) 3-Methoxyfuro[3,2-b]pyridine-2-carboxylic acid ethyl ester

The hydroxy is methylated according to the method in example 1a).
NMR ($^1$H, CDCl$_3$): 1.44 (t, J=7.2 Hz; 3H), 1.47 (q, J=7.2 Hz; 1H), 4.57 (s; 3H), 7.38 (dd, J=8.5, 4.6 Hz; 1H), 7.80 (dd, J=8.5, 1.0 Hz; 1H), 8.61 (dd, J=4.6, 1.0 Hz; 1H).

e) 3-Methoxyfuro[3,2-b]pyridine-2-carboxylic acid

This compound is obtained according to the same method as for example 1b).
FP=207° C.
NMR ($^1$H, DMSO-d$_6$): 4.42 (s; 3H), 7.56 (dd, J=8.6, 4.6 Hz; 1H), 8.12 (dd, J=8.6, 1.0 Hz; 1H), 8.65 (dd, J=4.6, 1.0 Hz; 1H), 13.39 (large; 1H).

f) 3-Methoxyfuro[3,2-b]pyridine-2-carboxylic acid (8-benzyl-8-azabicyclo[3.2.1]oct-3β-yl)amide dihydrochloride This compound is obtained according to the same method as for example 1c).
FP=172° C.
IR: 3420, 3048, 1732, 1665.
NMR (base; $^1$H, CDCl$_3$): 1.69 (m; 2H), 1.82 (m; 2H), 1.95 (m; 2H), 2.10 (m; 2H), 3.31 (m; 2H, H1 and H5), 3.65 (s; 2H, N—CH$_2$-Ph), 4.42 (m; 1H, H3), 4.57 (s; 3H, OCH$_3$), 6.80 (d, J=8.2 Hz; 1H, NH), 7.27 (m; 1H), 7.32 (m; 3H), 7.41 (d, J=7.3 Hz; 1H), 7.80 (dd, J=8.5, 0.73 Hz; 1H), 8.57 (d, J=4.0 Hz; 1H)

| Analysis: | C$_{23}$H$_{25}$N$_3$O$_3$ | Mass = 391.47 |
|---|---|---|
| | C$_{23}$H$_{25}$N$_3$O$_3$, 2 HCl | Mass = 464.39 |
| | C$_{23}$H$_{25}$N$_3$O$_3$, 2 HCl, 0.4 H$_2$O | Mass = 471.60 |

| | % C | % H | % N | % H$_2$O |
|---|---|---|---|---|
| calc. | 58.58 | 6.05 | 8.91 | 1.5 |
| detect. | 58.89 | 6.05 | 8.24 | 1.5 |

MS (DCI, NH$_3$): 392 (M$^+$+1; 100%)

EXAMPLE 5

3-Methoxyfuro[2,3-c]pyridine-2-carboxylic acid (8-benzyl-8-azabicyclo[3.2.1]oct-3β-yl)amide fumarate a) 3-Hydroxyfuro[2,3-c]pyridine-2-carboxylic acid ethyl ester

This compound is prepared as per J. Heterocycl. Chem. 1966, 3, 252, and J. Heterocycl. Chem. 1986, 23, 549.
FP=170° C.
NMR ($^1$H, CDCl$_3$): 1.48 (t, J=6.8 Hz; 3H), 4.52 (q, J=6.8 Hz; 3H), 7.70 (d, J=5.0 Hz; 1H), 8.52 (d, J=5.0 Hz; 1H), 8.94 (s; 1H)

b) 3-Methoxyfuro[2,3-c]pyridine-2-carboxylic acid ethyl ester

The hydroxy is methylated according to the method in example 1a).
NMR ($^1$H, CDCl$_3$): 1.45 (t, J=6.8 Hz; 3H), 4.29 (s; 3H), 4.48 (q, J=6.8 Hz; 2H), 7.73 (d, J=5.2 Hz; 1H), 8.48 (d, J=5.2 Hz; 1H), 8.96 (s; 1H).

c) 3-Methoxyfuro[2,3-c]pyridine-2-carboxylic acid

This compound is obtained according to the same method as for example 1b).
FP=260° C.
NMR ($^1$H, DMSO-d$_6$): 4.23 (s; 3H), 8.01 (d, J=5.4 Hz; 1H), 8.46 (d, J=5.4 Hz; 1H), 9.05 (s; 1H).

d) 3-Methoxyfuro[2,3-c]pyridine-2-carboxylic acid (8-benzyl-8-azabicyclo[3.2.1]oct-3β-yl)amide fumarate This compound is obtained according to the same method as for example 1c).
FP=101° C.
IR: 3377, 2976, 1706, 1655
NMR (base; $^1$H, CDCl$_3$): 1.66 (m; 2H), 1.77 (m; 2H), 1.94 (m; 2H), 3.29 (m; 2H, H1 and H5), 3.56 (s; 2H, N—CH$_2$-Ph), 4.29 (s; 3H, OCH$_3$), 4.43 (m; 1H, H3), 6.67 (d, J=8.3 Hz; 1H, NH), 7.26 (m; 1H), 7.33 (t, J=7.3 Hz; 21H), 7.39 (d, J=7.3 Hz; 2H), 7.68 (d, J=5.3 Hz; 1H), 8.45 (d, J=5.3 Hz; 1H), 8.93 (s; 1H)

| Analysis: | C$_{23}$H$_{25}$N$_3$O$_3$ | Mass = 391.47 |
|---|---|---|
| | C$_{23}$H$_{25}$N$_3$O$_3$, 1.5 C$_4$H$_4$O$_4$ | Mass = 565.58 |
| | C$_{23}$H$_{25}$N$_3$O$_3$, 1.5 C$_4$H$_4$O$_4$, 4 H$_2$O | Mass = 590.81 |

| | % C | % H | % N | % H$_2$O |
|---|---|---|---|---|
| calc. | 58.96 | 5.76 | 7.11 | 4.3 |
| detect. | 59.09 | 5.76 | 7.44 | 4.6 |

MS (ESI): 393 (M++1), 392 (M+, 100%)

EXAMPLE 6

3-Methoxyfuro[2,3-b]pyridine-2-carboxylic acid (8-benzyl-8-azabicyclo[3.2.1]oct-3β-yl)amide fumarate a) 3-Hydroxyfuro[2,3-b]pyridine-2-carboxylic acid ethyl ester

This compound is prepared as per J. Heterocycl. Chem. 1986, 23, 1465.
NMR ($^1$H, CDCl$_3$): 1.46 (t, J=7.2 Hz; 3H), 4.49 (q, J=7.2 Hz; 2H), 7.31 (dd, J=7.7, 4.8 Hz; 1H), 8.12 (dd, J=7.2, 1.6 Hz; 1H), 8.28 (large; 1H), 8.54 (dd, J=4.8, 1.6 Hz; 1H)

b) 3-Methoxyfuro[2,3-b]pyridine-2-carboxylic acid ethyl ester

The hydroxy is methylated according to the method in example 1a).

NMR ($^1$H, CDCl$_3$): 1.44 (t, J=6.8 Hz; 3H), 3.90 (s; 3H), 4.49 (q, J=7.2 Hz; 2H), 6.92 (dd, J=7.3, 5.0 Hz; 1H), 8.14 (dd, J=7.3, 1.3 Hz; 1H), 8.29 (dd, J=5.0, 1.3 Hz; 1H).

c) 3-Methoxyfuro[2,3-b]pyridine-2-carboxylic acid

This compound is obtained according to the same method as for example 1b).

FP=260° C.

NMR ($^1$H, DMSO-d$_6$): 4.24 (s; 3H), 7.45 (dd, J=7.4, 5.1 Hz; 1H), 8.52 (m; 2H).

d) 3-Methoxyfuro[2,3-b]pyridine-2-carboxylic acid (8-benzyl-8-azabicyclo[3.2.1]oct-3β-yl)amide fumarate This compound is obtained according to the same method as for example 1c).

FP=199° C.

IR: 3395, 1665, 1596

NMR (base; $^1$H, CDCl$_3$): 1.66 (m; 2H), 1.78 (m; 2H), 1.91 (m; 2H), 2.07 (m; 2H), 3.28 (m; 2H, H1 and H5), 3.56 (s; 2H, N—CH$_2$-Ph), 4.29 (s; 3H, OCH$_3$), 4.39 (m; 1H, H3), 6.56 (d, J=8.3 Hz; 1H, NH), 7.26 (m; 2H), 7.33 (t, J=7.3 Hz; 21H), 7.40 (d, J=7.3 Hz; 2H), 8.11 (dd, J=7.8, 1.6 Hz; 1H), 8.45 (dd, J=4.8, 1.6 Hz; 1H)

| Analysis: C$_{23}$H$_{25}$N$_3$O$_3$ | Mass = 391.47 |
| --- | --- |
| C$_{23}$H$_{25}$N$_3$O$_3$, C$_4$H$_4$O$_4$ | Mass = 507.54 |
| C$_{23}$H$_{25}$N$_3$O$_3$, C$_4$H$_4$O$_4$, 0.4 H$_2$O | Mass = 511.14 |

|  | % C | % H | % N | % H$_2$O |
| --- | --- | --- | --- | --- |
| calc. | 63.45 | 5.80 | 8.22 | 0.7 |
| detect. | 63.40 | 5.84 | 8.22 | 0.5 |

MS (ESI): 392 (M++1, 100%)

EXAMPLE 7

3-Methoxythieno[3,2-c]pyridine-2-carboxylic acid (8-benzyl-8-azabicyclo[3.2.1]oct-3β-yl)amide fumarate a) 4-Chloropyridine-3-carbaldehyde

This compound is prepared as per J. Heterocycl. Chem. 1988, 25, 81.

35.8 ml of n-BuLi (1.6 M in hexane; 57 mmol, 1 eq.) is added to a solution of 7.5 ml of N,N-diisopropylamine in 100 ml of tetrahydrofuran at −60° C. in nitrogen. The mixture is then left under stirring at 0° C. for 45 min before being cooled to −90° C. To this solution, a solution of 6.5 g of 4-chloropyridine (57 mmol, 1 eq.) in 25 ml of tetrahydrofuran is added drop by drop such that the temperature remains between −70 and −60° C. The mixture is left under stirring at −70° C. for 3 hrs. Then, a solution of 5.1 ml of ethylformate (63 mmol, 1.1 eq.) in 10 ml of tetrahydrofuran is added. The mixture is left under stirring for 1 hr at −65/−70° C. and the reaction mixture is then returned to −10° C. and hydrolysed with water. The organic phase is separated and the aqueous phase is extracted 3 times with ethyl acetate. The combined organic phases are dried on Na$_2$SO$_4$ and the solvent is evaporated.

5.91 g (73%) of formylated product is obtained.

NMR ($^1$H, CDCl$_3$/DMSO-d$_6$): 7.46 (d, J=5.6 Hz; 1H), 8.69 (d, J=5.6 Hz; 1H), 9.05 (s; 1H), 10.51 (s; 1H).

b) 4-Chloronicitinic acid

A mixture of the 5.9 g of product from step a) above, (42 mmol, 1 eq.) with 6.6 g of potassium permanganate (42 mmol, 1 eq.) in 200 ml of water is reflux heated for 3 hrs. The mixture is then hot-filtered and the residue is washed with 500 ml of hot water. The combined filtrate is concentrated to 50 ml, the pH is adjusted to 3 with 1N HCl and the solution is reconcentrated. This solution is placed at 4° C. for the crystallization of the product which is filtered and dried.

3.71 g (56%) of the desired acid is obtained.

NMR ($^1$H, CDCl$_3$/DMSO-d$_6$): 7.67 (d, J=4.8 Hz; 1H), 8.66 (d, J=4.8 Hz; 1H), 8.86 (s; 1H), 14.23 (large; 2H).

c) 4-Chloronicotinic acid ethyl ester (see J. Org. Chem. 1996, 26, 2257)

A solution of 1.5 g of sodium hydroxide (38 mmol, 1.6 eq.) in 8 ml of water is added to a solution of 3.71 g of the product from step b) above (23 mmol, 1 eq.) in 50 ml of hexamethylphosphorotriamide at 0° C. 7.5 ml of iodomethane (94 mmol, 4 eq.) is then introduced drop by drop for 1 hr. After that, the mixture is allowed to return to ambient temperature and left under stirring for 18 hrs. It is diluted with 400 ml of water and extracted 4 times with ethyl ether. The organic phase is washed thoroughly with water before drying on Na$_2$SO$_4$ and evaporating the solvent.

810 mg (18%) of the desired ester is obtained.

NMR ($^1$H, CDCl$_3$): 1.44 (t, J=7.2 Hz; 3H), 4.46 (q, J=7.2 Hz; 1H), 7.58 (d, J=5.6 Hz; 1H), 8.65 (d, J=5.6 Hz; 1H), 9.08 (s; 1H).

d) 3-Hydroxythieno[3,2-c]pyridine-2-carboxylic acid methyl ester

A mixture of 1.46 g of the product from step c) above (7.8 mmol, 1 eq.) with 0.7 ml of methyl thioglycolate (7.8 mmol, 1 eq.) in 100 ml of acetonitrile is reflux heated for 48 hrs in the presence of 1.6 g of potassium carbonate (11.8 mmol, 1.5 eq.). The mixture is allowed to return to ambient temperature and the solvent is evaporated. The residue is dissolved in water and acetic acid is added up to pH 4. The precipitate formed is filtered, washed with water and dried.

1.05 g (64%) of product is obtained.

FP=144° C.

NMR ($^1$H, CDCl$_3$): 3.98 (s; 3H), 7.68 (d, J=5.7 Hz; 1H), 8.59 (d, J=5.7 Hz; 1H), 9.22 (s; 1H), 10.14 (large; 1H).

e) 3-Methoxythieno[3,2-c]pyridine-2-carboxylic acid methyl ester

The hydroxy is methylated according to the method in example 1a).

NMR ($^1$H, CDCl$_3$): 3.94 (s; 3H), 4.24 (s; 3H), 7.67 (d, J=5.5 Hz; 1H), 8.56 (d, J=5.5 Hz; 1H), 9.17 (s; 1H)

f) 3-Methoxythieno[3,2-c]pyridine-2-carboxylic acid

This compound is obtained according to the same method as for example 1b).

NMR ($^1$H, DMSO-d$_6$): 4.45 (s; 3H), 8.04 (d, J=5.6 Hz; 1H), 8.57 (d, J=5.6 Hz; 1H), 9.13 (s; 1H), 13.61 (large; 1H)

g) 3-Methoxythieno[3,2-c]pyridine-2-carboxylic acid (8-benzyl-8-azabicyclo[3.2.1]oct-3β-yl)amide fumarate This compound is obtained according to the same method as for example 1c).

FP=201° C.

IR: 2372, 1702, 1644

NMR (base; $^1$H, CDCl$_3$): 1.73 (m; 2H), 1.80 (m; 2H), 1.96 (m; 2H), 2.11 (m; 2H), 3.33 (m; 2H, H1 and H5), 3.59 (s; 2H, N—CH$_2$-Ph), 4.12 (s; 3H, OCH$_3$), 4.40 (m; 1H, H3), 7.41 (d, J=7.2 Hz; 2H), 7.52 (d, J=5.6 Hz; 1H), 8.51 (d, J=5.6 Hz; 1H), 9.16 (s; 1H)

| | |
|---|---|
| Analysis: C$_{23}$ H$_{25}$ N$_3$ O$_2$ S | Mass = 407.54 |
| C$_{23}$ H$_{25}$ N$_3$ O$_2$ S, C$_4$ H$_4$ O$_4$ | Mass = 523.61 |
| C$_{23}$ H$_{25}$ N$_3$ O$_2$ S, 1.7 C$_4$ H$_4$ O$_4$, 0.23 H$_2$O | Mass = 609.09 |

| | % C | % H | % N | % H$_2$O |
|---|---|---|---|---|
| calc. | 58.76 | 5.37 | 6.90 | 0.7 |
| detect. | 58.53 | 5.48 | 7.21 | 0.7 |

MS (ESI): 430 (M$^+$+Na), 408 (M+, 100%)

EXAMPLE 8

3-Methoxythieno[2,3-b]pyridine-2-carboxylic acid [8-(4-chlorobenzyl)-8-azabicyclo[3.2.1]oct-3β-yl] amide hydrochloride a) t-Butyl-N-[8-(phenylmethyl)-8-azabicyclo[3.2.1] oct-3β-yl]carbamate At a normal temperature, a solution of 2.72 g of di-ter-butyldicarbonate (12.48 mmol, 1.2 eq.) in 10 ml of dichloromethane is added drop by drop to a solution of 2.25 g of 8-(phenylmethyl)-8-azabicyclo[3.2.1]octane-3β-amine (10.40 mmol, 1 eq.), prepared as per Eur. J. Med. Chem. 1984, 19, 105, in 20 mol of dichloromethane in the presence of 1.6 ml of triethylamine (11.44 mmol, 1.1 eq.). The mixture is left under stirring at ambient temperature until all the starting products have been used up. It is washed three times with water, dried and vacuum evaporated.

1.6 g (49%) of product is obtained after purification by filtration on silica followed by recrystallization in isopropyl ether.

FP=172-173° C.

NMR ($^1$H, CDCl$_3$): 1.43 (s; 9H), 1.48 (m; 2H), 1.65-1.85 (m; 4H), 2.02 (m; 2H), 3.19 (m; 2H, H1 and H5), 3.52 (s; 2H, N—CH$_2$-Ph), 3.81 (m; 1H, H3), 4.30 (m; 1H, NH-carbamate), 7.19-7.38 (m; 5H).

b) ter-Butyl-N-(8-azabicyclo[3.2.1]oct-3 β-yl)carbamate 1.6 g of ter-butyl-N-[8-(phenylmethyl)-8-azabicyclo [3.2.1]oct-3β-yl]carbamate (5.05 mmol, 1 eq.) dissolved in 80 ml of methanol is hydrogenated at atmospheric pressure at 45-50° C. in the presence of 0.1 g of 10% palladium-coated charcoal for 90 min. The catalyst is filtered, rinsed with methanol and vacuum evaporated.

1.1 g (97%) of the secondary amine product is obtained.

FP=123° C.

NMR ($^1$H, CDCl$_3$): 1.30 (m; 2H), 1.41 (s; 9H), 1.74 (m; 4H), 1.88 (m; 2H), 3.52 (m; 2H, H1 and H5), 3.78 (m; H1, H3), 4.34 (m; 1H; NH-carbamate)

c) ter-Butyl-[8-(4-chlorophenylmethyl)-8-azabicyclo [3.2.1]oct-3β-yl]carbamate

A mixture of 0.5 g of ter-butyl-N-(8-azabicycl[3.2.1]oct-3β-yl]carbamate (2.43 mmol, 1 eq.) and 0.4 g of 4-chlorobenzyl chloride (2.43 mmol, 1.1 eq.) in 30 ml of methylethylketone is reflux heated for 15 hrs in the presence of 1.45 g of cesium carbonate (4.4 mmol, 2 eq.) and 0.2 g of potassium iodide. The insoluble is filtered and rinsed with the solvent and vacuum evaporated. The product is taken up with dichloromethane, washed twice with water and vacuum evaporated.

0.45 g (58%) of the alkylation product is obtained after recrystallization in dichloromethane/petroleum ether.

FP=131-132° C.

d) 8-(4-Chlorophenylmethyl)-8-azabicyclo[3.2.1] octane-3β-amine

At a normal temperature, a solution of 3 ml of trifluoroacetic acid in 3 ml of dichloromethane is added drop by drop to a solution of 0.45 g of ter-butyl-N-[8-(4-chlorophenylmethyl)-8-azabicyclo[3.2.1]oct-3β-yl]carbamate (1.28 mmol, 1 eq.) in 12 ml of dichloromethane. After 4 hrs, the mixture is vacuum evaporated, taken up with 1N soda and extracted twice with dichloromethane. It is washed with water, dried and vacuum evaporated.

0.32 g of product with a quantitative yield is obtained.

NMR ($^1$H, CDCl$_3$): 1.47-1.73 (m; 6H), 1.96 (m; 2H), 2.93 (m, J=5.5 Hz; 1H), 3.13 (t, J=3.3 Hz; 2H), 3.49 (s; 2H), 7.26(m; 4H).

e) 3-Methoxythieno[2,3-b]pyridine-2-carboxylic acid [8-(4-chlorobenzyl)-8-azabicyclo[3.2.1]oct-3β-yl]amide hydrochloride This compound is prepared according to the method in example 1c).

FP=261° C.

IR: 3356, 1650, 1541

NMR (base; $^1$H, CDCl$_3$): 1.63 (m; 2H), 1.79 (m; 2H), 1.97 (m; 2H), 2.07 (m; 2H), 3.26 (m; 2H, H1 and H5), 3.51 (s; 2H, N—CH$_2$-aryl), 4.10 (s; 3H, OCH$_3$), 4.38 (m; 1H, H3), 7.26-7.36 (m; 5H), 8.09 (dd, J=8.3, 1.4 Hz; 1H), 8.66 (dd, J=4.6, 1.4 Hz; 1H)

| | |
|---|---|
| Analysis: C$_{23}$ H$_{24}$ Cl N$_3$ O$_2$ S | Mass = 441.98 |
| C$_{23}$ H$_{24}$ Cl N$_3$ O$_2$ S, HCl | Mass = 478.44 |

|  | % C | % H | % N |
|---|---|---|---|
| calc. | 57.74 | 5.27 | 8.78 |
| detect. | 57.92 | 5.26 | 8.72 |

MS (ESI): 444 (M++2), 442 (M+, 100%)

EXAMPLE 9

3-Methoxythieno[2,3-b]pyridine-2-carboxylic acid [8-(4-methoxybenzyl)-8-azabicyclo[3.2.1]oct-3β-yl] amide hydrochloride a) ter-Butyl-N-[8-(4-methoxyphenylmethyl)-8-azabicyclo[3.2.1]oct-3β-yl]carbamate A mixture of 0.7 g of 4-ter-butyl-N-(8-azabicyclo[3.2.1]oct-3β-yl)carbamate (3.0 mmol, 1 eq.), obtained in step b) of example 8, with 0.45 ml of 4-methoxybenzylchloride (3.3 mmol, 1.1 eq.) in 50 ml of acetonitrile is reflux heated for 20 hrs in the presence of cesium carbonate (6.0 mmol, 2 eq.) and 0.25 g of potassium iodide. The insoluble is filtered, rinsed with the solvent and vacuum evaporated. The mixture is taken up with dichloromethane, washed twice with water, dried and vacuum evaporated.

0.8 g (77%) of alkylation product is obtained.

FP=115° C.

NMR ($^1$H, CDCl$_3$): 1.41-1.55 (m; 2H), 1.43 (s; 9H, t-butyl), 1.65-1.79 (m; 4H), 1.98-2.04 (m; 2H), 3.19 (m; 2H, H1 and H5), 3.46 (s; 2H, N—CH$_2$—Ar), 3.80 (m; 4H, OCH$_3$ and H3), 4.30 (m; 1H, NH-carbamate), 6.86 (d, J=8.6 Hz; 2H), 7.27 (d, J=8.6 Hz; 2H).

b) 8-(4-Methoxyphenylmethyl)-8-azabicyclo[3.2.1]octane-3β-amine

At a normal temperature, 3 ml of trifluoroacetic acid is added drop by drop to a solution of 0.80 g of ter-Butyl-N-[8-(4-methoxyphenylmethyl)-8-azabicyclo[3.2.1]oct-3β-yl] carbamate (2.3 mmol, 1 eq.), obtained in the step above, in 20 ml of dichloromethane. After 3 hrs, the mixture is vacuum evaporated, taken up with 1N soda and extracted twice with dichloromethane. It is washed with water, dried and vacuum evaporated.

0.55 g (96.5%) of product is obtained.

FP<50° C.

NMR ($^1$H, DMSO-d$_6$): 1.29 (m; 2H), 1.42-1.55 (m; 4H), 1.88 (m; 2H), 2.78 (m; 1H, H3), 3.02 (m; 2H, H1 and H5), 3.40 (s; 2H, N—CH$_2$-aryl), 3.71 (s; OCH$_3$), 6.84 (d, J=8.7 Hz; 2H), 7.22 (d, J=8.7 Hz; 2H)

c) 3-Methoxythieno[2,3-b]pyridine-2-carboxylic acid [8-(4-methoxybenzyl)-8-azabicyclo[3.2.1]oct-3β-yl]amide hydrochloride This compound is prepared according to the method in example 1c), but with the corresponding reagents.

FP=231° C.

IR: 3397, 1651

NMR (base; $^1$H, CDCl$_3$): 1.67 (m; 2H), 1.79 (m; 2H), 1.95 (m; 2H), 2.10 (m; 2H), 3.31 (m; 2H, H1 and H5), 3.63 (s; 2H, N—CH$_2$-aryl), 3.81 (s; 3H, OCH$_3$), 4.09 (s; 3H, OCH$_3$), 4.40 (m; 1H, H3), 6.87 (d, J=8.6 Hz, 2H), 7.32 (m; 3H), 8.08 (dd, J=8.1, 1.4 Hz; 1H), 8.65 (dd, J=4.5, 1.4 Hz; 1H)

| Analysis: C$_{24}$H$_{27}$N$_3$O$_3$S | Mass = 437.56 |
|---|---|
| C$_{24}$H$_{27}$N$_3$O$_3$S, 0.5 HCl | Mass = 455.79 |
| C$_{24}$H$_{27}$N$_3$O$_3$S, 0.5 HCl, 0.1 H$_2$O | Mass = 457.79 |

|  | % C | % H | % N | % H$_2$O |
|---|---|---|---|---|
| calc. | 63.00 | 6.10 | 9.18 | 0.4 |
| detect. | 63.00 | 6.15 | 9.11 | 0.2 |

MS (ESI): 438 (M++1, 100%)

EXAMPLE 10

3-Methoxythieno[2,3-b]pyridine-2-carboxylic acid [8-cyclohexylmethyl-8-azabicyclo[3.2.1]oct-3β-yl] amide fumarate a) ter-Butyl-N-[8-cyclohexylmethyl-8-azabicyclo[3.2.1]oct-3β-yl]carbamate

A mixture of 0.7 g of 4-ter-butyl-N-(8-azabicyclo[3.2.1]oct-3β-yl)carbamate (3.0 mmol, 1 eq.), obtained in step b) of example 8, with 0.46 ml of bromomethylcyclohexane (3.3 mmol, 1 eq.) in 50 ml of methylethylketone is reflux heated for 20 hrs in the presence of cesium carbonate (6.0 mmol, 2 eq.) and 0.5 g of potassium iodide (3.0 mmol, 1 eq.). The insoluble is filtered, rinsed with the solvent and vacuum evaporated. It is taken up with dichloromethane, washed twice with water, dried and vacuum evaporated. 0.97 g of product with a quantitative yield is obtained.

FP=139-140° C.

NMR ($^1$H, CDCl$_3$): 0.85 (m; 2H), 1.04-13.5 (m; 4H), 1.40 (s; 9H), 1.41-1.89 (m; 13H), 2.10 (d, J=6.9 Hz; 2H, N—CH$_2$-cyclohexyl), 3.12 (m; 2H, H1 and H5), 3.74 (m; 1H, H3), 4.26 (m; 1H, NH-carbamate)

b) 8-(Cyclohexylmethyl)-8-azabicyclo[3.2.1]octane-3β-amine

At ambient temperature, 3 ml of trifluoroacetic acid is added drop by drop to a solution of 0.97 g of ter-butyl-N-[8-(cyclohexylmethyl)-8-azabicyclo[3.2.1]oct-3β-yl]carbamate (3.0 mmol, 1 eq.) in 15 ml of dichloromethane. After 2 hrs, the mixture is vacuum evaporated, taken up with 1N soda and extracted twice with dichloromethane. It is washed with water, dried and vacuum evaporated. 0.65 g (97%) of deprotection product is obtained.

NMR ($^1$H, CDCl$_3$): 0.7-1.87 (m; 21H), 2.15 (d, J=9.9 Hz; 2H, N—CH$_2$-cyclohexyl), 2.85 (m, J=5.6 Hz; 1H, H3), 3.10 (t, J=3.2 Hz; 2H, H1 and H5)

c) 3-Methoxythieno[2,3-b]pyridine-2-carboxylic acid [8-cyclohexylmethyl-8-azabicyclo[3.2.1]oct-3β-yl]amide fumarate This compound is prepared according to the method in example 1c).

FP=245° C.

IR: 3371, 1649, 1534

NMR (base; $^1$H, CDCl$_3$): 0.91 (m; 2H), 1.12-1.31 (m; 42H), 1.84 (m; 4H), 1.96 (m; 4H), 2.20 (m; 2H), 3.29 (m; 2H, H1 and H5), 4.10 (s; 3H, OCH$_3$), 4.38 (m; 1H, H3), 7.33 (dd, J=8.2, 4.6 Hz, 1H), 8.08 (dd, J=8.21, 1.34 Hz; 1H), 8.65 (dd, J=4.6, 1.3 Hz; 1H)

| Analysis: C$_{23}$ H$_{31}$ N$_3$ O$_2$ S | Mass = 413.59 |
| C$_{23}$ H$_{31}$ N$_3$ O$_2$ S, C$_4$ H$_4$ O$_4$ | Mass = 529.66 |

|  | % C | % H | % N |
| --- | --- | --- | --- |
| calc. | 61.23 | 6.66 | 7.93 |
| detect. | 61.31 | 6.75 | 7.96 |

MS (ESI): 414.3 (M+; 100%)

EXAMPLE 11

3-Methoxythieno[2,3-b]pyridine-2-carboxylic acid [(8-(4-fluorobenzyl)-8-azabicyclo[3.2.1]oct-3β-yl)]amide hydrochloride Using the same starting materials as for example 8, but with the corresponding reagents, the following intermediates are obtained:

a) t-Butyl-N-[8-(4-fluorobenzyl)-8-azabicyclo[3.2.1]oct-3β-yl]carbamate

NMR ($^1$H, CDCl$_3$): 1.43 (s; 9H), 1.46 (m; 2H), 1.68 (m; 2H), 1.82 (m: 2H), 2.00 (m; 2H), 3.17 (m; 2H), 3.48 (s; 2H), 3.79 (m; 1H, H3), 4.30 (m; 1H, NH-carbamate), 6.97 (d, J=8.7 Hz; 1H), 6.99 (d, J=8.7 Hz; 1H), 7.30 (dd, J=8.7, 2.7 Hz; 2H)

b) 8-(4-Fluorobenzyl)-8-azabicyclo[3.2.1]octane-3β-amine

NMR ($^1$H, DMSO-d6): 1.32 (m; 2H), 1.49-1.57 (m; 4H), 1.90 (m; 2H), 2.79 (septett, J=5.7 Hz; 3H), 3.04 (m; 2H), 3.47 (s; 2H), 7.10 (d, J=8.4 Hz; 1H), 7.13 (d, J=8.4 Hz; 1H), 7.36 (dd, J=8.4, 5.9 Hz; 2H)

c) 3-Methoxythieno[2,3-b]pyridine-2-carboxylic acid [(8-(4-fluorobenzyl)-8-azabicyclo[3.2.1]oct-3β-yl)]amide hydrochloride This compound is prepared according to the method in example 1c), but with the corresponding reagents.

FP=247° C.

IR: 3371, 1679, 1536

NMR (base; $^1$H, CDCl$_3$): 1.63 (m; 2H), 1.79 (m; 2H), 1.96 (m; 2H), 2.07 (m; 2H), 3.26 (m; 2H, H1 and H5), 3.64 (s; 2H, N—CH2-aryl), 4.09 (s; 3H, OCH$_3$), 4.39 (m; 1H, H3), 7.02 (m; 2H), 7.35 (m; 3H), 8.09 (dd, J=8.1, 1.5 HZ; 1H), 8.65 (dd, J=4.6, 1.5 Hz; 1H)

| Analysis: C$_{23}$ H$_{24}$ F N$_3$ O$_2$ S | Mass = 425.53 |
| C$_{23}$ H$_{24}$ F N$_3$ O$_2$ S, HCl | Mass = 461.99 |
| C$_{23}$ H$_{24}$ F N$_3$ O$_2$ S, 0.84 HCl, 0.14 H$_2$O | Mass = 458.67 |

|  | % C | % H | % N | % H$_2$O |
| --- | --- | --- | --- | --- |
| calc. | 60.23 | 5.52 | 9.16 | 0.55 |
| detect. | 60.22 | 5.47 | 9.14 | 0.6 |

MS (ESI): 447.9 (M$^+$+H2O), 425.9 (M$^+$, 100%)

EXAMPLE 12

3-Methoxythieno[2,3-b]pyridine-2-carboxylic acid [8-thiophen-3-ylmethyl-8-azabicyclo[3.2.1]oct-3β-yl]amide hydrochloride a) 3-Bromomethylthiophene

This mixture is described in: Org. Synth. Coil, Vol. IV, 1963, 921.

A mixture of 4.4 g of 3-methylthiphene (44.8 mmol, 1 eq.) and 7.15 g of N-bromosuccinimide (40 mmol, 0.9 eq.) is reflux heated for 2 hrs in the presence of 0.1 g of benzoyl peroxide in 100 ml of tetrachloromethane. The insoluble is filtered, the mixture is vacuum evaporated and purified by vacuum distillation. 1.2 g of brominated product is obtained.

NMR ($^1$H, CDCl$_3$): 4.51 (s; 2H), 7.10 (d, J=4.5 Hz; 1H), 7.27 (d, J=1.8 Hz; 1H), 7.29 (dd, J=4.5, 1.8 Hz; 1H).

Using the same starting materials as for example 8, but with the corresponding reagents, the following intermediates are obtained:

a) t-Butyl-N-[8-(3-thienylmethyl)-8-azabicyclo[3.2.1]oct-3β-yl]carbamate 0.9 g of product (63%) is obtained after crystallization in isopropyl ether/petroleum ether.

FP=138° C.

NMR ($^1$H, CDCl$_3$): 1.45-1.56 (m; 2H), 1.44 (s; 9H, t-butyl), 1.60-1.85 (m; 2H), 1.99 (m; 2H), 3.22 (m; 2H, H1 and H5), 3.54 (s; 2H, N—CH$_2$—Ar), 3.78 (m; 1H, H3), 4.30 (m; 1H, NH-carbamate), 7.07-7.12 (m; 2H), 7.24-7.29 (m; 1H)

c) 8-(3-Thienylmethyl)-8-azabicyclo[3.2.1]oct-3β-amine 0.50 g of amine (86%) is obtained.

NMR ($^1$H, DMSO-d$_6$): 1.25-1.36 (m; 4H), 1.43-1.59 (m; 4H), 1.85-1.91 (m; 2H), 2.78 (m; 1H, H3), 3.07 (t, J=3.0 Hz; 2H, H1 and H5), 3.48 (s; 2H, N—CH$_2$—Ar), 7.06 (d, J=4.9 Hz; 1H), 7.26 (d, J=2.8 Hz; 1H), 7.44 (dd, J=4.9, 2.8 Hz; 1H)

d) 3-Methoxythieno[2,3-b]pyridine-2-carboxylic acid [8-thiophen-3-ylmethyl-8-azabicyclo[3.2.1]oct-3β-yl]amide hydrochloride This compound is prepared according to the method in example 1c), but with the corresponding reagents.

FP=230° C.

IR: 3385, 1641, 1534

NMR (base; $^1$H, CDCl$_3$): 1.63 (m; 2H), 1.78 (m; 2H), 1.97 (m; 2H), 2.08 (m; 2H), 3.32 (m; 2H, H1 and H5), 3.57 (s; 2H, N—CH$_2$-aryl), 4.09 (s; 3H, OCH$_3$), 4.39 (m; 1H, H3), 7.14 (m; 2H), 7.29-7.35 (m; 3H), 8.08 (dd, J=8.1, 1.5 HZ; 1H), 8.65 (dd, J=4.7, 1.5 Hz; 1H)

| | | |
|---|---|---|
| Analysis: $C_{21}H_{23}N_3O_2S_2$ | | Mass = 413.56 |
| $C_{21}H_{23}N_3O_2S_2$, HCl | | Mass = 450.02 |
| $C_{21}H_{23}N_3O_2S_2$, 0.85 HCl, 0.24 $H_2O$ | | Mass = 448.67 |

| | % C | % H | % N | % $H_2O$ |
|---|---|---|---|---|
| calc. | 56.20 | 5.46 | 9.36 | 0.9 |
| detect. | 56.21 | 5.82 | 8.87 | 1.1 |

MS (ESI): 436 ($M^+$+NA), 414 ($M^+$+1; 100%)

EXAMPLE 13

3-Methoxythieno[2,3-c]pyridine-2-carboxylic acid (8-benzyl-8-azabicyclo[3.2.1]oct-3β-yl]amide fumarate a) 3-Bromo-4-picoline This reagent is described in Bull. Soc. Chim. Fr. 1976, 530.
Stirring well, 31 ml of 4-picoline (0.322 mol, 1 eq.) is added drop by drop to 107 g of aluminum chloride (0.805 mol, 2.5 eq.) in a 1 l three-necked flask equipped. with a cooling apparatus in nitrogen. 9.9 ml of bromine (0.193 mol, 0.6 eq.) is then introduced progressively, while keeping the temperature at 95-100° C. The mixture is left under stirring at this temperature for 18 hrs, 6.6 ml of bromine (0.129 mol, 0.4 eq.) is added and stirring is continued for 4 hrs. After that, the reaction medium is poured into 1000 ml of ice, soda is added until the inorganic salts have dissolved. The oily phase is retrieved, the aqueous phase is extracted 3 times with ethyl ether and the combined organic phase is washed with a sodium bisulfite solution and then with water. Drying is performed on $Na_2SO_4$ and the solvent is evaporated.
10.68 g (19%) of the brominated product is obtained after purification by flash chromatography on silica (eluent: ethyl acetate/petroleum ether=1/1).
NMR ($^1H$, CDCl$_3$): 2.40 (s; 3H), 7.17 (d, J=4.9 Hz; 1H), 8.37 (d, J=4.9 Hz; 1H), 8.64 (s; 1H)

b) 3-Bromoisonicotinic acid

A mixture of 10.68 g of the product from the previous step (62 mmol, 1 eq.) with 29.4 g of potassium permanganate (186 mmol, 3 eq.) in 100 ml of water is reflux heated. The manganese oxide formed is hot-filtered, the precipitate is washed with boiling water and the filtrate is retrieved. The filtrate is allowed to return to ambient temperature, extracted 3 times with ethyl ether and the aqueous phase is acidified with HCl (pH 2-3). The solution is concentrated to a volume of 50 ml and kept at 4° C. for 2 hrs. The crystals formed are filtered, washed with water and dried. 3.98 g of product (32%) is obtained.
FP=240° C.
NMR ($^1H$, DMSO-d$_6$): 4.39 (large; 1H), 7.70 (d, J=4.9 Hz; 1H), 8.67 (d, H=4.9 Hz; 1H), 8.88 (s; 1H).

c) 3-Bromoisonicotinic methyl ester

A mixture of 3.98 g of the acid obtained in the previous step (20 mmol, 1 eq.) in 50 ml of methanol is reflux heated in the presence of 4 ml of concentrated sulfuric acid. The mixture is allowed to return to ambient temperature and extracted 3 times with ethyl acetate. The organic phase is dried on $Na_2SO_4$ and the solvent is evaporated. 2.65 g (62%) of esterified product is obtained.
NMR ($^1H$, CDCl$_3$): 4.02 (s; 3H), 7.64 (d, J=4.9 Hz; 1H), 8.63 (d, J=4.9 Hz; 1H), 8.88 (s; 1H).

d) 3-Hydroxythieno[2,3-c]pyridine-2-carboxylic acid methyl ester

A mixture of 2.65 g of the product from the previous step (12 mmol, 1 eq.) with 1.1 ml of methyl thioglycolate (12 mmol, 1 eq.) in 100 ml of acetonitrile is reflux heated for 18 hrs in the presence of 2.54 g of potassium carbonate (18 mmol, 1.5 eq.). After that, the mixture is allowed to return to ambient temperature, the solvent is evaporated and the residue is dissolved in water. A few ml of acetic acid (pH 4) are added and the precipitate formed is filtered. It is vacuum dried. 1.51 g (59%) of aromatized product is obtained.
NMR ($^1H$, CDCl$_3$): 4.00 (s; 3H), 7.63 (d, J=4.9 Hz; 1H), 8.58 (d, J=4.9 Hz; 1H), 9.10 (s; 1H), 10.02 (s; 1H).

e) 3-Methoxythieno[2,3-c]pyridine-2-carboxylic acid methyl ester

The compound is prepared according to the method in example 1a).
NMR ($^1H$, CDCl$_3$): 3.96 (s; 3H), 4.18 (s; 3H), 7.74 (d, J=5.5 Hz; 1H), 8.56 (d, J=5.5 Hz; 1H), 9.09 (s; 1H)

f) 3-Methoxythieno[2,3-c]pyridine-2-carboxylic acid

The compound is prepared according to the method in example 1b).
NMR ($^1H$, CDCl$_3$): 4.10 (s; 3H), 7.83 (d, J=5.5 Hz; 1H), 8.55 (d, J=5.5 Hz; 1H), 9.27 (s; 1H), 13.72 (large; 1H).

g) 3-Methoxythieno[2,3-c]pyridine-2-carboxylic acid (8-benzyl-8-azabicyclo[3.2.1]oct-3β-yl]amide fumarate The compound is prepared according to the method in example 1c).
FP=173° C.
IR: 3372, 1697, 1646, 1534
NMR (base; $^1H$, CDCl$_3$): 1.65 (m; 2H), 1.78 (m; 2H), 1.97 (m; 2H), 2.11 (m; 2H), 3.30 (m; 2H, H1 and H5), 3.55 (s; 2H, N—CH$_2$-Ph), 4.12 (s; 3H, OCH$_3$), 4.39 (m; 1H, H3), 7.26 (m; 1H), 7.34 (m; 2H), 7.39 (d, J=7.2 Hz; 2H), 7.67 (d, J=5.6 Hz; 1H), 8.53 (d, J=5.6 Hz; 1H), 9.10 (s; 1H).

| | | |
|---|---|---|
| Analysis: $C_{23}H_{25}N_3O_2S$ | | Mass = 407.54 |
| $C_{23}H_{25}N_3O_2S$, $C_4H_4O_4$ | | Mass = 523.61 |
| $C_{23}H_{25}N_3O_2S$, $C_4H_4O_4$, 0.1 $H_2O$ | | Mass = 571.75 |

| | % C | % H | % N | % $H_2O$ |
|---|---|---|---|---|
| calc. | 60.10 | 5.43 | 7.35 | 0.3 |
| detect. | 60.10 | 5.46 | 7.21 | 0.3 |

MS (ESI): 430 ($M^+$+Na), 408 ($M^+$+1; 100%)

EXAMPLE 14

3-Isopropoxythieno[2,3-b]pyridine-2-carboxylic acid (8-benzyl-8-azabicyclo[3.2.1]oct-3β-yl]amide fumarate a) 3-Isopropoxythieno[2,3-b]pyridine-2-carboxylic acid methyl ester 1.04 g of 3-hydroxythieno[2,3-b]pyridine-2-carboxylic acid methyl ester (5.0 mmol, 1 eq.), obtained as per J. Heterocycl. Chem. 1987, 24, 85, is added to a solution of 2.8 g of potassium ter-butylate (25 mmol, 5 eq.) in 15 ml of DMSO at 0° C. in nitrogen. After 30 min, 2.35 ml of 2-bromopropane is added. After 2 hrs of stirring at ambient temperature, the mixture is heated at 100° C. for 8 hrs. It is allowed to return to ambient temperature, the reaction medium is poured onto 200 ml of water and extracted twice with ethyl acetate. The organic phase is washed with sodium chloride-saturated water, drying is performed on $Na_2SO_4$ and the solvent is evaporated.

880 mg (70%) of O-alkylation product is obtained.

NMR ($^1$H, CDCl$_3$): 1.43 (d, J=6.0 Hz; 6H), 3.93 (s; 3H), 4.86 (septett, J=6.0 Hz; 1H), 7.30 (dd, J=8.0, 4.4 Hz; 1H), 8.10 (d, J=8.0, 1.4 Hz; 1H), 8.56 (d, J=4.4, 1.4 Hz; 1H)

b) 3-Isopropoxythieno[2,3-b]pyridine-2-carboxylic acid

This compound is obtained according to the same method as for example 1b).

NMR ($^1$H, DMSO-d$_6$): 1.31 (d, J=6.0 Hz; 6H), 4.83 (septett, J=6.0 Hz; 1H), 7.52 (d, J=8.1, 4.6 Hz; 1H), 8.26 (d, J=8.1 Hz; 1H), 8.74 (d, J=4.6 Hz; 1H), 13.43 (large; 1H).

c) 3-Isopropoxythieno[2,3-b]pyridine-2-carboxylic acid (8-benzyl-8-azabicyclo[3.2.1]oct-3β-yl]amide fumarate This compound is obtained according to the same method as for example 1c).

FP=184° C.

IR: 3390, 1649, 1535

NMR (base; $^1$H, CDCl$_3$): 1.44 (d, J=6.4 Hz; 6H, CH—(CH$_3$)$_2$), 1.66 (m; 2H), 1.78 (m; 2H), 1.96 (m; 2H), 2.09 (m; 2H), 3.29 (m; 2H, H1 and H5), 3.57 (s; 2H, N—CH$_2$-Ph), 4.74 (septett, J=6.4 Hz; 1H, CH—(CH$_3$)$_2$), 7.26 (m; 1H), 7.31 (m; 3H), 7.39 (d, J=7.3 Hz; 1H), 8.01 (dd, J=8.2, 1.5 Hz; 1H), 8.44 (dd, J=4.6, 1.5 Hz; 1H).

| Analysis: $C_{25}H_{29}N_3O_2S$ | Mass = 435.59 |
|---|---|
| $C_{25}H_{29}N_3O_2S, C_4H_4O_4$ | Mass = 551.67 |

| | % C | % H | % N |
|---|---|---|---|
| calc. | 63.14 | 6.03 | 7.62 |
| detect. | 62.96 | 6.06 | 7.64 |

MS (ESI): 437 (M$^+$+2), 436 (M$^+$+1; 100%)

EXAMPLE 15

3-Ethoxythieno[2,3-b]pyridine-2-carboxylic acid (8-benzyl-8-azabicyclo[3.2.1]oct-3β-yl)amide fumarate a) 3-Ethoxythieno[2,3-b]pyridine-2-carboxylic acid methyl ester

This compound is prepared according to the method in example 14a), but with the corresponding reagent, ethyl iodide.

NMR ($^1$H, CDCl$_3$): 1.52 (t, J=7.2 Hz; 3H), 3.93 (s; 3H), 4.18 (q, J=7.2 Hz; 2H), 7.28 (dd, J=8.0, 4.5 Hz; 1H), 8.06 (dd, J=8.0, 1.3 Hz; 1H), 8.57 (dd, J=4.5, 1.3 Hz; 1H).

b) 3-Ethoxythieno[2,3-b]pyridine-2-carboxylic acid

This compound is obtained according to the same method as for example 1b).

FP=206° C.

NMR ($^1$H, DMSO-d$_6$): 1.37 (t, J=6.8 Hz; 3H), 4.37 (q, J=6.8 Hz; 2H), 7.53 (dd, J=7.8, 4.6 Hz; 1H), 8.28 (d, J=7.8 Hz; 1H), 8.74 (d, J=4.6 Hz; 1H), 13.47 (large; 1H).

c) 3-Ethoxythieno[2,3-b]pyridine-2-carboxylic acid (8-benzyl-8-azabicyclo[3.2.1]oct-3β-yl)amide fumarate This compound is obtained according to the same method as for example 1c).

FP=170° C.

IR: 3357, 1685, 1536

NMR (base; $^1$H, CDCl$_3$): 1.51 (t, J=7.2 Hz; 3H, CH$_2$—CH$_3$), 1.65 (m; 2H), 1.78 (m; 2H), 1.97 (m; 2H), 2.10 (m; 2H), 3.28 (m; 2H, H1 and H5), 3.56 (s; 2H, N—CH$_2$-Ph), 4.35 (q, J=7.2 Hz; 2H, O—CH—CH$_2$—CH$_3$), 4.38 (m; 1H, H3), 7.26 (m; 1H), 7.33 (m; 3H), 7.39 (d, J=7.2 Hz; 2H), 8.04 (dd, J=6.7, 1.5 Hz; 1H), 8.64 (dd, J=4.6, 1.5 Hz; 1H).

| Analysis: $C_{24}H_{27}N_3O_2S$ | Mass = 421.56 |
|---|---|
| $C_{24}H_{27}N_3O_2S, C_4H_4O_4$ | Mass = 537.63 |
| $C_{24}H_{27}N_3O_2S, C_4H_4O_4, 1/3 H_2O$ | Mass = 543.63 |

| | % C | % H | % N | % $H_2O$ |
|---|---|---|---|---|
| calc. | 61.87 | 5.87 | 7.73 | 1.1 |
| detect. | 61.96 | 5.81 | 7.65 | 1.1 |

MS (ESI): 422 (M$^+$+1; 100%)

EXAMPLE 16

3-Methoxyfuro[3,2-b]pyridine-2-carboxylic acid [8-(4-fluorobenzyl)-8-azabicyclo[3.2.1]oct-3β-yl] amide hydrochloride a) 3-Methoxyfuro[3,2-b]pyridine-2-carboxylic acid [8-azabicyclo[3.2.1]oct-3β-yl]amide A solution of 1.49 g of ammonium formate (22 mmol, 4 eq.) in 6 ml of water is added to a solution of 2.15 g of 3-methoxyfuro[3,2-b]pyridine-2-carboxylic acid [8-benzyl- 8-azabicyclo[3.2.1]oct-3β-yl]amide (5.49 mmol, 1 eq.), obtained in example 4f), in 50 ml of methanol. 200 mg of Pd(OH)$_2$/C is added and reflux heating is performed for 18 hrs. The mixture is allowed to return to ambient temperature, the catalyst is filtered and the solvent evaporated. The residue is taken up with dichloromethane, washed twice with water followed by extraction with 3 times 100 ml of 1N HCl. The extract is alkalinized with soda (pH 10) and extracted 3 times with dichloromethane. Drying is performed, the solvent is evaporated and purified by flash chromatography on silica (eluent: dichloromethane/methanol/ammonia=95/4.5/0.5). 1.73 g (85%) of debenzylation product is obtained.

NMR ($^1$H, CDCl$_3$): 1.61 (m; 2H), 1.89 (m; 2H), 2.05 (m; 2H), 2.08 (m; 2H), 2.40 (large; 1H), 3.68 (m; 2H), 4.44 (m; 1H, H3), 4.56 (s; 3H), 6.81 (d, J=8.5 Hz; 1H), 7.32 (dd, J=8.5, 4.6 Hz; 1H), 8.81 (dd, J=8.5, 1.2 Hz; 1H), 8.57 (dd, J=4.6, 1.2 Hz; 1H).

b) 3-Methoxyfuro[3,2-b]pyridine-2-carboxylic acid [8-(4-fluorobenzyl)-8-azabicyclo[3.2.1]oct-3β-yl] amide hydrochloride A mixture of 580 mg of the product from the previous step (1.9 mmol, 1 eq.) with 0.24 ml of 4-fluorobenzyl bromide (1.9 mmol, 1 eq.) in 50 ml of methylethylketone is reflux heated for 18 hrs in the presence of 270 mg of potassium carbonate (1.9 mmol) and 50 mg of potassium iodide. After that, the mixture is allowed to return to ambient temperature and the solvent is evaporated. The residue is taken up with dichloromethane and washed 3 times with water. The organic phase is dried, the solvent is evaporated and purified by flash chromatography on silica (eluent: dichloromethane).

370 mg of product (47%) is obtained in base form for which the salt is then formed with a stoechiometric quantity of an HCl solution in isopropanol.

FP=242° C.
IR: 3367, 1670, 1540
NMR (base; $^1$H, CDCl$_3$): 1.65 (m; 2H), 1.83 (m; 2H), 1.95 (m; 2H), 3.26 (m; 2H), 3.52 (s; 2H, N—CH$_2$-Ph), 4.40 (m; 1H, H3), 4.57 (s; 3H, OCH$_3$), 6.77 (d, J=8.3 Hz; 1H, NH), 7.01 (t, J=8.6 Hz; 2H), 7.32 (dd, J=8.4, 4.5 Hz, 1H), 7.36 (m; 2H), 7.79 (d, J=8.4 Hz; 1H), 8.57 (d, J=4.5 Hz; 1H).

| Analysis: C$_{23}$ H$_{24}$ F N$_3$ O$_3$ | Mass = 409.46 |
| C$_{23}$ H$_{24}$ F N$_3$ O$_3$, HCl | Mass = 445.92 |
| C$_{23}$ H$_{24}$ F N$_3$ O$_3$, 1.1 HCl, 0.1 H$_2$O | Mass = 451.37 |

| | % C | % H | % N | % H$_2$O |
|---|---|---|---|---|
| calc. | 61.20 | 5.65 | 9.31 | 0.4 |
| detect. | 61.09 | 5.65 | 9.11 | 0.4 |

EXAMPLE 17

3-Methoxyfuro[3,2-b]pyridine-2-carboxylic acid [8-(4-chlorobenzyl)-8-azabicyclo[3.2.1]oct-3β-yl] amide hydrochloride This derivative is obtained according to the method in example 16, but with the corresponding reagents.
FP=232° C.
IR: 3392, 1675, 1540
NMR ($^1$H, CDCl$_3$): 1.62 (m; 2H), 1.81 (dd, J=14.0, 6.0 Hz; 2H), 1.95 (m; 2H), 2.06 (m; 2H), 3.25 (m; 2H), 3.52 (s; 2H, N—CH$_2$-Ph), 4.39 (m; 1H, H3), 4.57 (s; 3H, OCH$_3$), 6.77 (d, J=8.2 Hz; 1H, NH), 7.28-7.35 (m; 5H), 7.79 (dd, J=8.4, 1.0 Hz; 1H), 8.57 (dd, J=4.5, 1.0 Hz; 1H).

| Analysis: C$_{23}$ H$_{24}$ Cl N$_3$ O$_3$ | Mass = 425.92 |
| C$_{23}$ H$_{24}$ Cl N$_3$ O$_3$, HCl | Mass = 462.38 |
| C$_{23}$ H$_{24}$ Cl N$_3$ O$_3$, HCl, 0.13 H$_2$O | Mass = 464.72 |

| | % C | % H | % N | % H$_2$O |
|---|---|---|---|---|
| calc. | 59.45 | 5.35 | 8.86 | 0.5 |
| detect. | 59.46 | 5.38 | 8.82 | 0.5 |

EXAMPLE 18

3-Methoxyfuro[3,2-b]pyridine-2-carboxylic acid (8-cyclohexylmethyl-8-azabicyclo[3.2.1]oct-3β-yl) amide hydrochloride This derivative is obtained according to the method in example 16, but with the corresponding reagents.
FP=217° C.
IR: 3291, 1659, 1537
NMR ($^1$H, CDCl$_3$): 0.91 (m; 2H), 1.12-1.35 (m; 3H), 1.37 (m; 1H), 1.62-1.85 (m; 7H), 1.86 (m; 2H), 1.89-1.97 (m; 4H), 2.16 (d, J=6.8 Hz; 2H), 3.23 (m; 2H), 4.35 (m; 1H, H3), 4.56 (s; 3H, OCH$_3$), 6.76 (d, J=8.2 Hz; 1H, NH), 7.33 (dd, J=8.4, 4.5 Hz; 1H), 7.79 (dd, J=8.4 Hz; 1H), 8.56 (d, J=4.5 Hz; 1H).

| Analysis: C$_{23}$ H$_{31}$ N$_3$ O$_3$ | Mass = 397.52 |
| C$_{23}$ H$_{31}$ N$_3$ O$_3$, HCl | Mass = 433.98 |
| C$_{23}$ H$_{31}$ N$_3$ O$_3$, HCl, 0.17 H$_2$O | Mass = 437.02 |

| | % C | % H | % N | % H$_2$O |
|---|---|---|---|---|
| calc. | 63.21 | 7.46 | 9.61 | 0.7 |
| detect. | 62.93 | 7.46 | 9.27 | 0.7 |

MS (ESI, 250° C.): 398 (M$^+$; 100%)

EXAMPLE 19

3-Methoxythieno[2,3-b]pyridine-2-carboxylic acid [8-butyl-8-azabicyclo[3.2.1]oct-3β-yl]amide fumarate This compound is prepared according to the method in example 8, but using the corresponding reagents.

a) t-Butyl-N-[8-butyl-8-azabicyclo[3.2.1]oct-3β-yl] carbamate

NMR ($^1$H, CDCl$_3$): 0.91 (t, J=7.6 Hz; 3H), 1.30 (p, J=7.6 Hz; 2H), 1.43 (s; 9H), 1.40-1.48 (m; 4H), 1.63 (m; 2H), 1.79 (m; 2H), 1.92 (m; 2H), 2.31 (d, J=7.6 Hz; 1H), 2.33 (d, J=7.6 Hz; 1H), 3.24 (m; 2H), 3.78 (m; 1H, H3), 4.28 (large; 1H, NH-carbamate).

b) 8-Butyl-8-azabicyclo[3.2.1]octane-3β-amine

NMR ($^1$H, DMSO-$d_6$): 0.87 (t, J=7.2 Hz; 3H), 1.23-1.35 (m; 6H), 1.43 (m; 2H), 1.48 (m; 2H), 1.77 (m; 2H), 2.27 (t, J=7.2 Hz; 2H), 2.75 (septett, J=5.6 Hz; 1H, H3), 3.03 (m; 2H).

c) 3-Methoxythieno[2,3-b]pyridine-2-carboxylic acid [8-butyl-8-azabicyclo[3.2.1]oct-3β-yl]amide fumarate FP=211° C.
IR: 3374, 1641, 1536
NMR (salt; $^1$H, CD$_3$OD): 1.02 (t, J=7.6 Hz; 3H), 1.45 (sextett, J=7.6 Hz; 2H), 1.74 (m; 2H), 2.10-2.31 (m; 6H), 2.33 (m; 2H), 3.10 (m; 2H), 4.02 (m; 2H), 4.20 (m; 2H), 4.46 (m; 1H, H3), 6.69 (s; 2H, fumaric acid), 7.50 (dd, J=8.3, 4.7 Hz; 1H), 8.40 (dd, J=8.3, 1.5 Hz; 1H), 8.65 (dd, J=4.7, 1.5 Hz; 1H).

| Analysis: $C_{20}H_{27}N_3O_2S$ | Mass = 373.52 |
| --- | --- |
| $C_{20}H_{27}N_3O_2S, C_4H_4O_4$ | Mass = 489.60 |

|  | % C | % H | % N |
| --- | --- | --- | --- |
| calc. | 58.88 | 6.38 | 8.58 |
| detect. | 58.90 | 6.41 | 8.56 |

MS (ESI): 374.2 (M$^+$, 100%)

EXAMPLE 20

3-Methoxyfuro[2,3-b]pyrazine-2-carboxylic acid (8-benzyl-8-azabicyclo[3.2.1]oct-3β-yl)amide hydrochloride a) 3-Chloro-2-pyrazine methyl carboxylate (J. Chem. Soc. Perkin Trans. I, 1996, 247)

In 20 ml of concentrated hydrochloric acid, 3.06 g (20 mmol, 1 eq.) of 3-amino-2-pyrazine methyl carboxylate is introduced at 0° C. A solution of 1.52 g (22 mmol, 1.1 eq.) of NaNO2 in 15 ml of water is then introduced drop by drop, while limiting the temperature to <5° C., until the gaseous emission stops. The solution obtained is filtered and added slowly to a sodium acetate solution (20 g) in 40 ml of water at 0° C. Stirring is maintained for 15 min, and then acidified with concentrated HCl. Extraction (4 times 30 ml of ethyl acetate) gives 1.35 g of chlorinated compound after drying and evaporation.

NMR ($^1$H, CDCl$_3$): 4.05 (s; 3H; OCH3), 8.54 (d, J=2.4 Hz; 1H; arom. H), 8.60 (d, J=2.4 Hz; 1H; arom. H).

b) 3-Hydroxy-2-ethoxycaronylfuro[2,3-b]pyrazine

A solution of 17.4 ml (0.184 mmol, 2.8 eq.) of ethyl glycolate in 20 ml of DME is added drop by drop to a suspension of 6.85 g (0.171 mol, 2.6 eq.) of NaH (60% in oil) at 0° C. in 200 ml of DME. After leaving under stirring for 15 min, 11.36 g of the chlorinated derivative from step a) above in solution in 20ml of DME is then introduced. After returning to a normal temperature, the medium is heated to 80° C. for 9 hrs. After evaporation and resuspension in water, the medium is acidified with acetic acid to pH 4 and then extracted with 5 times 50 ml of ethyl acetate. After drying on Na2So4, filtration and evaporation, the residue is triturated in petroleum ether and then crystallized, filtered and vacuum dried. 9.91 g (72%) of aromatization product is obtained. FP=160° C. (dec).

NMR ($^1$H, CDCl$_3$): 1.48 (t; J=7.2 Hz; 3H; CH3 ester), 4.53 (q; J=7.2 Hz; 2H; CH2 ester), 8.41 (m; 1H; OH), 8.50 (d, J=2.4 Hz; 1H; arom. H), 8.69 (d, J=2.4 Hz; 1H; arom. H).

c) 3-Methoxy-2-ethoxycarbonylfuro[2,3-b]pyrazine

This compound is prepared according to the method in example 1a).

Yield=76%.

NMR ($^1$H, CDCl$_3$): 1.44 (t; J=7.2 Hz; 3H; CH3 ester), 4.48 (q; J=7.2 Hz; 2H, CH2 ester), 4.58 (s; 3H; OCH3), 8.46 (D, j=2.4 Hz; 1H; arom. H), 8.64 (d, J=2.4 Hz; 1H; arom. H).

d) 3-Methoxyfuro[2,3-b]pyrazine-2-carboxylic acid

This compound is prepared according to the method in example 1b).

Yield=82%, FP=242° C.

NMR ($^1$H, DMSO d6): 4.43 (s; 3H, OCH3), 8.60 (d, J=2.4 Hz; 1H; arom. H), 8.79 (d, J=2.4 Hz; 1H; arom. H).

e) 3-Methoxyfuro[2,3-b]pyrazine-2-carboxylic acid (8-benzyl-8-azabicyclo[3.2.1]oct-3β-yl)amide hydrochloride This compound is prepared according to the method in example 1c), but using the corresponding reagents. It is obtained with a 69% yield after flash chromatography on silica and chromatography on alumina.

Salt Preparation:

1.12 g of the base (2.8 mmol, 1 eq.) obtained is dissolved in 5 ml of acetone. 0.75 ml of an isopropanol—3.6N HCl solution (2.8 mmol, 1 eq.) is introduced. The mixture is vacuum evaporated, taken up with acetone, the salt formed is filtered and dried.

Yield: 1.02g (83%).

FP=222° C.

IR: 3359, 1670.9, 1542.7

NMR (base; $^1$H, CDCl$_3$): 1.65 (m; 2H), 1.78 (m; 2H), 1.95 (m; 2H), 2.09 (m; 2H), 3.29 (m; 2H, H1 and H5), 3.56 (s; 2H, N CH$_2$Ph), 4.38 (m; 1H, H3), 4.55 (s; 3H; OCH3), 6.70 (m; 1H; NH), 7.26-7.40 (m; 5H; Ph), 8.40 (d, J=2.4 Hz; 1H; arom. H), 8.59 (d, J=2.4 Hz; 1H; arom. H).

| Analysis: | | | | |
| --- | --- | --- | --- | --- |
| $C_{22}H_{24}N_4O_3$, HCl, 0.036 H$_2$O | | | Mass = 429.570 | |

|  | % C | % H | % N | % H$_2$O |
| --- | --- | --- | --- | --- |
| calc. | 61.51 | 5.88 | 13.04 | 0.15 |
| detect. | 61.26 | 5.88 | 12.70 | 0.15 |

MS (ESI): 393.2 (M$^+$; 100%)

EXAMPLE 21

3-Methoxyfuro[2,3-b]pyrazine-2-carboxylic acid [8-(4-chlorobenzyl)-8-azabicyclo[3.2.1]oct-3β-yl) amide hydrochloride This compound is prepared according to the method in example 1c), but using the corresponding reagents, i.e. 3-methoxyfuro[2,3-b]pyrazine-2-carboxylic acid described in example 20d) and the amine described in example 8d).

1.32 g (47%) of a white foam is obtained after flash chromatography on silica and chromatography on alumina (eluent CH2Cl2).

The hydrochloride is prepared in acetone by adding isopropanol—HCl.

1.27 g (89%) of hydrochloride is obtained.

FP=231° C.

IR: 3385.5, 1677.8, 1541.7

NMR (base; $^1$H, CDCl$_3$): 1.63 (m; 2H), 1.79 (m; 2H), 1.95 (m; 2H), 2.07 (m; 2H), 3.24 (m; 2H, H1 and H5), 3.51 (s; 2H, N CH$_2$Ph), 4.39 (m; 1H, H3), 4.55 (s; 3H; OCH3), 6.68 (m; 1H; NH), 7.26-7.34 (m; 4H; Ph), 8.40 (d, J=2.4 Hz; 1H; arom. H), 8.60 (d, J=2.4 Hz; 1H; arom. H).

| Analysis: | |
|---|---|
| $C_{22} H_{24} N_4 Cl O_3$, HCl, 0.08 $H_2O$ | Mass = 464.808 |

|  | % C | % H | % N | % H$_2$O |
|---|---|---|---|---|
| calc. | 56.85 | 5.24 | 12.05 | 0.31 |
| detect. | 56.94 | 5.32 | 12.01 | 0.32 |

MS (ESI): 497.2 (M$^+$; 100%)

EXAMPLE 22

3-Methoxyfuro[2,3-b]pyrazine-2-carboxylic acid [8-(4-fluorobenzyl)-8-azabicyclo[3.2.1]oct-3β-yl) amide hydrochloride This compound is prepared according to the method in example 1c), but using the corresponding reagents, i.e. 3-methoxyfuro[2,3-b]pyrazine-2-carboxylic acid described in example 20d) and the amine described in example 11b).

780 mg (46%) of a white foam is obtained after flash chromatography on silica and chromatography on alumina (eluent CH2Cl2).

The hydrochloride is prepared in acetone by adding isopropanol—HCl.

710 mg (84%) of hydrochloride is obtained.

FP=234° C.

IR: 3401.6, 1670.5, 1521.9

NMR (base; $^1$H, CDCl$_3$): 1.63 (m; 2H), 1.79 (m; 2H), 1.94 (m; 2H), 2.07 (m; 2H), 3.25 (m; 2H, H1 and H5), 3.51 (s; 2H, N CH$_2$Ph), 4.40 (m; 1H, H3), 4.55 (s; 3H; OCH3), 6.68 (m; 1H; NH), 7.01 (m; 2H; J=8.4 Hz; Ph), 7.34 (m; 2H; J=7.64 Hz; J'=5.6 Hz; Ph), 8.40 (d, J=2.4 Hz; 1H; arom. H), 8.59 (d, J=2.4 Hz; 1H; arom. H).

| Analysis: | |
|---|---|
| $C_{22} H_{23} N_4 F O_3$, HCl, 0.19 $H_2O$ | Mass = 450.335 |

|  | % C | % H | % N | % H$_2$O |
|---|---|---|---|---|
| calc. | 58.68 | 5.46 | 12.44 | 0.77 |
| detect. | 58.62 | 5.43 | 12.30 | 0.78 |

MS (ESI): 411.2 (M$^+$, 100%)

EXAMPLE 23

3-Methoxyfuro[2,3-b]pyrazine-2-carboxylic acid [8-thiophen-2-ylmethyl-8-azabicyclo[3.2.1]oct-3β-yl]amide hydrochloride a) ter-Butyl-N-[8-(2-thienylmethyl)-8-azabicyclo [3.2.1]oct-3β-yl]carbamate 4.52 g (0.02 mol) of the ter-Butyl-N-(8-azabicyclo[3.2.1] oct-3β-yl)carbamate intermediate, obtained in example 8b), is dissolved at 0° C. in a nitrogen atmosphere in 100 ml of CH2CL2, with 2.25 g (0.02 mol) of 2-thiophene carboxaldehyde and 1.8 ml of acetic acid. 7 g (1.6 eq.) of NaBH(OAc)3 is then introduced in portions at this temperature. After leaving under stirring overnight at ambient temperature, the medium is poured into water (50 ml) and extracted twice with CH2Cl2. After drying on Na2SO4, filtration and evaporation, the residue is triturated with a 1N NaOH solution and the crystals obtained are dewatered, washed with water and then vacuum dried. 4.85 g (75%) of product is obtained.

FP=155° C.

NMR ($^1$H, CDCl$_3$): 1.43 (s; 9H, t-butyl), 1.45 (m; 2H), 1.69 (m; 2H), 1.82 (m; 2H), 1.98 (m; 2H), 3.26 (m; 2H, H1 and H5), 3.70 (s; 2H, N—CH$_2$-thioph), 3.79 (m; 1H, H3), 4.32 (m; 1H, NH-carbamate), 6.87 (m; 1H), 6.98 (m; 1H), 7.20 (m; 1H)

b) 8-(2-Thienylmethyl)-8-azabicyclo[3.2.1]oct-3β-amine

This compound is obtained according to the same method as in example 8d).

NMR ($^1$H, DMSO-d$_6$): 1.28-1.34 (m; 42H), 1.47-1.57 (m; 4H), 1.85-1.89 (m; 2H), 2.78 (m; 1H, H3), 3.12 (t, J=3.0 Hz; 2H, H1 and H5), 3.67 (s; 2H, N—CH$_2$-thioph), 6.94 (m; 2H; H thioph), 7.36 (m; 1H; H thioph).

c) 3-Methoxyfuro[2,3-b]pyrazine-2-carboxylic acid [8-thiophen-2-ylmethyl-8-azabicyclo[3.2.1]oct-3β-yl)amide hydrochloride This compound is prepared according to the method in example 1c), but using the corresponding reagents, i.e. 3-methoxyfuro[2,3-b]pyrazine-2-carboxylic acid described in example 20d) and the amine obtained in step b) above.

White crystals with a 52% yield are obtained. FP=143° C.

The hydrochloride is prepared in ethanol by adding isopropanol—HCl.

The hydrochloride is obtained with a 48% yield.

FP=230° C. (dec.).

IR: 3360, 1672.8, 1547.7

NMR (base; $^1$H, CDCl$_3$): 1.63-1.69 (m; 2H), 1.79 (m; 2H), 1.93-1.98 (m; 2H), 2.05 (m; 2H), 3.34 (m; 2H, H1 and H5), 3.73 (s; 2H, N CH$_2$-thioph), 4.34-4.45 (m; 1H, H3), 4.56 (s; 3H; OCH3), 6.69 (d; 1H; NH), 6.90-6.96 (m; 2H; thioph), 7.23 (m; 1H; thioph), 8.40 (d, J=2.4 Hz; 1H; arom. H), 8.59 (d, J=2.4 Hz; 1H; arom. H).

Analysis:

C$_{20}$ H$_{22}$ N$_4$ O$_3$ S HCl, 0.19 H$_2$O        Mass = 434.95

|  | % C | % H | % N |
|---|---|---|---|
| calc. | 55.23 | 5.33 | 12.88 |
| detect. | 55.33 | 5.36 | 12.70 |

MS (ESI): 399.26 (M$^+$, 100%)

EXAMPLE 24

3-Methylsulfanylfuro[2,3-b]pyrazine-2-carboxylic acid (8-benzyl-8-azabicyclo[3.2.1]oct-3β-yl)amide hydrochloride a) 3-(Diethoxyphosphoryloxy)furo[2,3-b]pyrazine-2-carboxylic acid ethyl ester This compound is obtained according to the method in example 2a), from 3-hydroxy-2-ethoxycarbonylfuro[2,3-b]pyrazine, with a quantitative yield, in the form of a red oil, migrating in TLC on silica with an Rf=0.46 in the ethyl acetate-petroleum ether system (80-20).

b) 3-Methylsulfanylfuro[2,3-b]pyrazine-2-carboxylic acid ethyl ester

The raw product from step a) above is treated according to the method in example 2b) to give an ester which is used in the next step with no purification.

c) 3-Methylsulfanylfuro[2,3-b]pyrazine-2-carboxylic acid

This derivative is obtained according to the method in example 1b) to give, with a 48% yield, the desired acid. Rf=0.11 on silica TLC, elution: CH2Cl2-Methanol 90-10.
NMR ($^1$H, DMSO-d$_6$): 2.94 (s; 3H; SCH3), 8.62 (d, J=2.3 Hz; 1H; arom. H), 8.78 (d, J=2.3 Hz; 1H; arom. H).

d) 3-Methylsulfanylfuro[2,3-b]pyrazine-2-carboxylic acid (8-benzyl-8-azabicyclo[3.2.1]oct-3β-yl)amide hydrochloride This compound is prepared according to the method in example 1c), but using the corresponding reagents. It is obtained with a 38% yield after flash chromatography on silica and chromatography on alumina (elution: CH2Cl2), in the form of a pale yellow foam.
Salt preparation:
0.63 g of the base (1.5 mmol) obtained is dissolved in 5 ml of acetone. A stoechiometric quantity of an isopropanol—3.6N HCl solution is introduced. The mixture is vacuum evaporated, taken up with acetone, the salt formed is filtered and dried. 520 mg of pale yellow crystals are obtained.
Yield 76%.
FP=150° C.
IR: 3426, 3237, 1649, 1552.
NMR (HCl; $^1$H, CD3OD): 2.11-2.27 (m; 6H), 2.50 (m; 2H), 2.94 (s; 3H; SCH$_3$), 4.00 (m; 2H, H1 and H5), 4.25 (s; 2H, N—CH$_2$-Ph), 4.50 (m; 1H, H3), 7.50 (m; 3H; Ph), 7.63 (m; 2H; Ph), 8.47 (d, J=2.4 Hz; 1H; arom. H), 8.67 (d, J=2.4 Hz; 1H; arom. H).

Analysis:

C$_{22}$ H$_{24}$ N$_4$ O$_2$ S, 0.3 HCl, 0.35 H$_2$O        Mass = 462.22

|  | % C | % H | % N | % H$_2$O |
|---|---|---|---|---|
| calc. | 57.16 | 5.67 | 12.12 | 1.36 |
| detect. | 57.35 | 5.74 | 11.51 | 1.47 |

MS (ESI): 409.2 (M$^+$, 100%)

EXAMPLE 25

3-Methylsulfanylfuro[2,3-b]pyrazine-2-carboxylic acid [8-(4-chlorobenzyl)-8-azabicyclo[3.2.1]oct-3β-yl]amide hydrochloride This compound is prepared according to the method in example 1c), but using the corresponding reagents. It is obtained with a 26% yield after flash chromatography on silica and chromatography on alumina (elution: CH2Cl2), in the form of a pale yellow foam. TLC on silica gives an Rf=0.26 (elution: CH2CL2-MeOH 95-5).
Salt Preparation:
The base obtained is dissolved in acetone. A stoechiometric quantity of an isopropanol—3.6N HCl solution is introduced. The mixture is vacuum evaporated, taken up with acetone, triturated, and the salt formed is filtered and dried. Pale yellow crystals are obtained. 87% yield.
FP=173° C.
IR: 3398, 3255, 1652, 1560.
NMR (base; $^1$H, CDCl$_3$): 1.67 (m; 2H), 1.78 (m; 2H), 1.93 (m; 2H), 2.07 (m; 2H), 2.93 (s; 3H; SCH3); 3.25 (m; 2H, H1 and H5), 3.53 (s; 2H, N—CH$_2$Ph), 4.40 (m; 1H, H3), 6.69 (d; 1H, NH), 7.29 (d; 2H; J=8.4 Hz; Ph), 7.34 (d; 2H; J=8.4 Hz; Ph), 8.41 (d, J=2.4 Hz; 1H; arom. H), 8.63 (d, J=2.4 Hz; 1H; arom. H).

Analysis:

C$_{22}$ H$_{24}$ N$_4$ O$_2$ S, HCl, 1.14 H$_2$O        Mass = 499.969

|  | % C | % H | % N | % H$_2$O |
|---|---|---|---|---|
| calc. | 52.85 | 5.30 | 11.21 | 4.28 |
| detect. | 52.44 | 5.34 | 11.01 | 4.29 |

MS (ESI): 443.2 (M$^+$, 100%).

EXAMPLE 26

3-Methylsulfanylfuro[2,3-b]pyrazine-2-carboxylic acid [8-(4-fluorobenzyl)-8-azabicyclo[3.2.1]oct-3β-yl]amide hydrochloride This compound is prepared according to the method in example 1c), but using the corresponding reagents. It is obtained with a 48% yield after flash chromatography on silica and chromatography on alumina (elution: CH2Cl2), in the form of a pale yellow foam. TLC on silica gives an Rf=0.32 (elution: CH2CL2-MeOH 95-5).

The base obtained is dissolved in acetone. A stoechiometric quantity of an isopropanol—3.6N HCl solution is introduced. The mixture is vacuum evaporated, taken up with acetone, triturated, and the salt formed is filtered and then dried. Pale yellow crystals are obtained. 69% yield.

FP=182° C.
IR: 3421, 3235, 1648, 1553.
NMR (base; $^1$H, CDCl$_3$): 1.72 (m; 2H), 1.79 (m; 2H), 1.92 (m; 2H), 2.09 (m; 2H), 2.93 (s; 3H; SCH3); 3.26 (m; 2H, H1 and H5), 3.54 (s; 2H, N—CH$_2$Ph), 4.40 (m; 1H, H3), 6.71 (d; 1H, NH), 7.01 (d; 2H; J=8.6 Hz; Ph), 7.36 (dd; 2H; J=8.0 Hz and 5.8 Hz; Ph), 8.41 (d, J=2.5 Hz; 1H; arom. H), 8.62 (d, J=2.5 Hz; 1H; arom. H).

| Analysis: | | | | |
|---|---|---|---|---|
| $C_{22}H_{23}FN_4O_2S$, 1.1 HCl, 0.75 $H_2O$ | | | Mass = 480.096 | |
| | % C | % H | % N | % $H_2O$ |
| calc. | 55.04 | 5.37 | 11.67 | 2.89 |
| detect. | 54.74 | 5.28 | 11.42 | 2.91 |

MS (ESI): 427.2 (M$^+$, 100%).

EXAMPLE 27

3-Methoxythieno[2,3-b]pyrazine-2-carboxylic acid (8-benzyl-8-azabicyclo[3.2.1]oct-3β-yl)amide hydrochloride a) 3-Hydroxy-2-methoxycarbonylthieno[2,3-b]pyrazine

The mixture of 1.35 g (7.8 mmol, 1 eq.) of 3-chloro-2-pyrazine methyl carboxylate prepared in example 20a), 0.7 ml (7.8 mmol, 1 eq.) of methyl thioglycolate and 1.62 g (11.7 mmol, 1.5 eq.) of K2CO3 in 60 ml of acetonitrile is heated under stirring for 16 hrs. The solvent is concentrated and immersed in 200 ml of water. After acidifying with 1N HCl, extraction is performed 3 times with CH2Cl2, the organic phase is dried on Na2CO3, filtered and evaporated. 1.21 g (73.5%) of aromatized product is obtained. FP=188° C.

NMR ($^1$H, DMSO): 2.50 (s; 3H; SCH3), 3.87 (s; OCH3), 8.81 (d, J=2.3 Hz; 1H, arom. H), 8.86 (d, J=2.3 Hz; 1H; arom. H), 11.67 (m; 1H; OH).

b) 3-Methoxy-2-methoxycarbonylthieno[2,3-b]pyrazine

This compound is prepared according to the method in example 1a).
Yield=33%. FP=104° C.

NMR ($^1$H, CDCl$_3$): 3.96 (s; 3H; OCH3 ester), 4.46 (s; 3H; OCH3), 8.63 (d, J=2.3 Hz; 1H; arom. H), 8.70 (d, J=2.3 Hz; 1H; arom. H).

c) 3-Methoxythieno[2,3-b]pyrazine-2-carboxylic acid

This compound is prepared according to the method in example 1b).
Yield=85%.
NMR ($^1$H, DMSO d$_6$): 4.30 (s; 3H; OCH3), 8.80 (d, J=2.2 Hz; 1H; arom. H), 8.86 (d, J=2.2 Hz; 1H; arom. H).

d) 3-Methoxythieno[2,3-b]pyrazine-2-carboaxylic acid (8-benzyl-8-azabicyclo[3.2.1]oct-3β-yl)amide hydrochloride This compound is prepared according to the method in example 1c), but using the corresponding reagents. It is obtained with a 68% yield after flash chromatography on silica (elution CH2Cl2-MeOH 95-5).

Salt Preparation:
The base obtained is dissolved in ethyl acetate. A stoechiometric quantity of an isopropanol—5N HCl solution is introduced. After trituration and crystallization, the salt formed is filtered and dried. Yield 94%.

FP=241° C.
IR: 3360, 2957, 2366, 1644, 1536.
NMR (base; $^1$H, CDCl$_3$): 1.68 (m; 2H), 1.79 (m; 2H), 1.96 (m; 2H), 2.10 (m; 2H), 3.30 (m; 2H, H1 and H5), 3.56 (s; 2H, N CH$_2$Ph), 4.37 (m; 1H, H3), 4.50 (s; 3H; OCH3), 6.70 (m; 1H; NH), 7.19-7.43 (m; 5H; Ph), 8.56 (d, J=2.3 Hz; 1H; arom. H), 8.62 (d, J=2.3 Hz; 1H; arom. H).

| Analysis: $C_{22}H_{24}N_4O_2S$, HCl | | Mass = 444.99 | |
|---|---|---|---|
| $C_{22}H_{24}N_4O_2S$, HCl, 0.11 $H_2O$ | | Mass = 446.97 | |

| | % C | % H | % N | % $H_2O$ |
|---|---|---|---|---|
| calc. | 59.12 | 5.69 | 12.53 | 0.44 |
| detect. | 59.11 | 5.76 | 12.30 | 0.45 |

MS (ESI): 409.20 (M$^+$, 100%).

EXAMPLE 28

3-Methoxythieno[2,3-b]pyrazine-2-carboxylic acid [8-(4-chlorobenzyl)-8-azabicyclo[3.2.1]oct-3β-yl] amide hydrochloride This compound is prepared according to the method in example 1c), but using the corresponding reagents. It is obtained with a 58% yield after flash chromatography on silica (CH2CL2-MeOH 99-1 elution), in the form of a foam. Rf=0.31 (TLC on silica, eluent: CH2CL2-MeOH 95-5).

Salt Preparation:
The base obtained is dissolved in ethyl acetate. A stoechiometric quantity of an isopropanol—5N HCl solution is introduced. After trituration and crystallization, the salt formed is filtered and dried. Yield 87%.

FP=234° C.
IR: 3366, 3032, 2434, 1645, 1534

NMR (base; $^1$H, CDCl$_3$): 1.67 (m; 2H), 1.79 (m; 2H), 1.95 (m; 2H), 2.07 (m; 2H), 3.25 (m; 2H, H1 and H5), 3.51 (s; 2H, N CH$_2$Ph), 4.38 (m; 1H, H3), 4.51 (s; 3H; OCH3), 7.28-7.35 (m; 4H; Ph), 7.40 (m; 1H; NH), 8.56 (d, J=2.3 Hz; 1H; arom. H), 8.63 (d, J=2.3 Hz; 1H; arom. H).

| Analysis: C$_{22}$H$_{23}$Cl N$_4$O$_2$S, HCl | Mass = 479.43 |
|---|---|
| C$_{22}$H$_{23}$Cl N$_4$O$_2$S, HCl, 0.15 H$_2$O | Mass = 482.13 |

|  | % C | % H | % N | % H$_2$O |
|---|---|---|---|---|
| calc. | 54.81 | 5.08 | 11.62 | 0.56 |
| detect. | 54.64 | 5.33 | 11.30 | 0.55 |

MS (ESI): 443.1 (M$^+$, 100%).

EXAMPLE 29

3-Methoxythieno[2,3-b]pyrazine-2-carboxylic acid [8-(4-fluorobenzyl)-8-azabicyclo[3.2.1]oct-3β-yl] amide hydrochloride This compound is prepared according to the method in example 1c), but using the corresponding reagents. It is obtained with an 80% yield after flash chromatography on silica (CH2CL2-MeOH 99-1 elution), in the form of a foam. Rf=0.17 (TLC on silica, eluent: CH2CL2-MeOH 95-5).

Salt Preparation:

The base obtained is dissolved in ethyl acetate. A stoechiometric quantity of an isopropanol—5N HCl solution is introduced. After trituration and crystallization, the salt formed is filtered and dried. Yield 87%.

FP=233° C.

IR: 3369, 2499, 2465, 2432, 1644, 1533

NMR (base; $^1$H, CDCl$_3$): 1.64 (m; 2H), 1.79 (m; 2H), 1.96 (m; 2H), 2.08 (m; 2H), 3.26 (m; 2H, H1 and H5), 3.51 (s; 2H, N CH$_2$Ph), 4.38 (m; 1H, H3), 4.50 (s; 3H; OCH3), 7.01 (t; J=8.5 Hz; 2H; Ph), 7.33-7.41 (m; 3H; NH and Ph), 8.56 (d, J=2.3 Hz; 1H; arom. H), 8.625 (d, J=2.3 Hz; 1H; arom. H).

| Analysis: C$_{22}$H$_{23}$F N$_4$O$_2$S, HCl | Mass = 479.439 |
|---|---|
| C$_{22}$H$_{23}$F N$_4$O$_2$S, HCl, 0.12 H$_2$O | Mass = 465.14 |

|  | % C | % H | % N | % H$_2$O |
|---|---|---|---|---|
| calc. | 56.81 | 5.25 | 12.04 | 0.47 |
| detect. | 56.58 | 5.36 | 11.67 | 0.48 |

MS (ESI): 427.19 (M$^+$, 100%).

EXAMPLE 30

3-Methylsulfanylthieno[2,3-b]pyrazine-2-carboxylic acid (8-benzyl-8-azabicyclo[3.2.1]oct-3β-yl)amide hydrochloride a) 3-(Diethoxyphosphoryloxy)thieno[2,3-b]pyrazine-2-carboxylic acid methyl ester This compound is obtained according to the method in example 2a), from the product in example 27a), with a 46% yield, in the form of an oil, migrating in TLC on silica with an Rf=0.33 in the ethyl acetate-petroleum ether system (50-50).

b) 3-Methylsulfanylthieno[2,3-b]pyrazine-2-carboxylic acid methyl ester

The raw product from step a) above is treated according to the method in example 2b) to give an ester which is used in the next step with no purification.

c) 3-Methylsulfanylthieno[2,3-b]pyrazine-2-carboxylic acid

This derivative is obtained according to the method in example 1b) to give, with a 90% yield, the desired acid. Rf=0.19 on silica TLC, elution: CH2Cl2-Methanol 90-10.

NMR ($^1$H, DMSO d$_6$): 2.88 (s; 3H; SCH3), 8.81 (d, J=2.3 Hz; 1H; arom. H), 8.87 (d, J=2.3 Hz; 1H; arom. H).

d) 3-Methylsulfanylthieno[2,3-b]pyrazine-2-carboxylic acid (8-benzyl-8-azabicyclo[3.2.1]oct-3β-yl) amide hydrochloride This compound is prepared according to the method in example 1c), but using the corresponding reagents. It is obtained with a 49% yield after flash chromatography on silica and chromatography on alumina (elution: CH2Cl2), in the form of pale yellow crystals.

Salt Preparation:

The base obtained is dissolved in ethyl acetate, a stoechiometric quantity of an isopropanol—5N HCl solution is introduced. The mixture is vacuum evaporated, taken up with ethyl acetate, the salt formed is filtered and dried. Pale yellow crystals are obtained. Yield 89%.

FP=249° C.

NMR (base; $^1$H, CDCl$_3$): 1.80 (m; 4H), 1.99 (m; 2H), 2.11 (m; 2H), 2.64 (s; 3H; SCH3), 3.31 (m; 2H, H1 and H5), 3.57 (s; 2H, N—CH$_2$Ph), 4.42 (m; 1H, H3), 7.24-7.46 (m; 5H; Ph), 8.62 (d, J=2.3 Hz; 1H; arom. H), 8.64 (m; 1H; NH), 8.75 (d, J=2.3 Hz; 1H; arom. H).

| Analysis: C$_{22}$H$_{24}$N$_4$O S$_2$, HCl | Mass = 461.05 |
|---|---|
| C$_{22}$H$_{24}$N$_4$O S$_2$, HCl, 0.074 H$_2$O | Mass = 462.38 |

|  | % C | % H | % N | % H$_2$O |
|---|---|---|---|---|
| calc. | 57.15 | 5.48 | 12.12 | 0.29 |
| detect. | 57.05 | 5.37 | 11.96 | 0.29 |

MS (ESI): 425.1 (M$^+$, 100%).

EXAMPLE 31

3-Methylsulfanylthieno[2,3-b]pyrazine-2-carboxylic acid [8-(4-chlorobenzyl)-8-azabicyclo[3.2.1]oct-3β-yl]amide hydrochloride This compound is prepared according to the method in example 1c), but using the corresponding reagents. It is obtained with a 38% yield after flash chromatography on silica (CH2CL2-MeOH 99-1 elution), in the form of a foam. Rf=0.39 (TLC on silica, eluent: CH2CL2-MeOH 95-5).

Salt Preparation:

The base obtained is dissolved in ethyl acetate. A stoechiometric quantity of an isopropanol—5N HCl solution is introduced. After trituration and white crystals have been obtained, the salt formed is filtered and dried. Yield 68%.

FP=236° C.

IR: 3466, 3254, 2515, 1654, 1637, 1545

NMR (base; $^1$H, CDCl$_3$): 1.65-1.81 (m; 4H), 2.00 (m; 2H), 2.09 (m; 2H), 2.65 (s; 3H, SCH3), 3.27 (m; 2H, H1 and H5), 3.53 (s; 2H, N CH$_2$Ph), 4.41 (m; 1H, H3), 7.30 (d; J=8.3 Hz; 2H; Ph), 7.34 (d; J=8.3 Hz, 2H; Ph), 8.2 (d, J=2.3 Hz; 1H; arom. H), 8.63 (m; 1H; NH), 8.76 (d, J=2.3 Hz; 1H; arom. H).

| Analysis: $C_{22}H_{23}ClN_4OS_2$, HCl | Mass = 495.50 |
|---|---|
| $C_{22}H_{23}ClN_4OS_2$, HCl, 0.38 H$_2$O | Mass = 502.34 |

| | % C | % H | % N | % H$_2$O |
|---|---|---|---|---|
| calc. | 52.60 | 4.97 | 11.15 | 1.38 |
| detect. | 52.44 | 5.16 | 10.98 | 1.39 |

MS (ESI): 459.1 (M$^+$, 100%).

EXAMPLE 32

3-Methylsulfanylthieno[2,3-b]pyrazine-2-carboxylic acid [8-(4-fluorobenzyl)-8-azabicyclo[3.2.1]oct-3β-yl]amide hydrochloride This compound is prepared according to the method in example 1c), but using the corresponding reagents. It is obtained with a 38% yield after flash chromatography on silica (CH2CL2-MeOH 99-1 elution), in the form of a foam. Rf=0.20 (TLC on silica, eluent: CH2CL2-MeOH 95-5).

Salt Preparation:

The base obtained is dissolved in ethyl acetate. A stoechiometric quantity of an isopropanol—5N HCl solution is introduced. After trituration and white crystals have been obtained, the salt formed is filtered and dried. Yield 86%.

FP=221° C.

IR: 3426, 32393, 3169, 3051, 2972, 1636, 1608, 1560

NMR (base; $^1$H, CDCl$_3$): 1.57-1.81 (m; 4H), 1.99 (m; 2H), 2.09 (m; 2H), 2.64 (s; 3H, SCH3), 3.28 (m; 2H, H1 and H5), 3.52 (s; 2H, N CH$_2$Ph), 4.40 (m; 1H, H3), 7.01 (d; J=8.5 Hz; 2H; Ph), 7.36 (dd; J=5.9 Hz, 2H; Ph), 8.62 (d, J=2.3 Hz; 1H; arom. H), 8.62 (m; 1H; NH), 8.75 (d, J=2.3 Hz; 1H; arom. H).

| Analysis: $C_{22}H_{23}FN_4OS_2$, HCl | Mass = 479.04 |
|---|---|
| $C_{22}H_{23}FN_4OS_2$, HCl, 0.35 H$_2$O | Mass = 485.35 |

| | % C | % H | % N | % H$_2$O |
|---|---|---|---|---|
| calc. | 54.44 | 5.13 | 11.54 | 1.32 |
| detect. | 54.23 | 5.40 | 11.40 | 1.31 |

MS (ESI): 443.16 (M$^+$, 100%).

EXAMPLE 33

3-Methylsulfanylthieno[2,3-b]pyrazine-2-carboxylic acid [8-thiophen-2-ylmethyl-8-azabicyclo[3.2.1]oct-3β-yl)amide hydrochloride a) ter-Butyl-N-[8-(thiophen-2-ylmethyl)-8-azabicyclo[3.2.1]oct-3β-yl]carbamate 4.52 g (0.02 mmol) of the ter-Butyl-N-(8-azabicyclo[3.2.1]oct-3β-yl)carbamate intermediate, obtained in example 8b), is dissolved at 0° C. in a nitrogen atmosphere in 100 ml of CH2CL2, with 2.25 g (0.02 mol) of 2-thiophene carboxaldehyde and 1.8 ml of acetic acid. 7 g (1.6 eq.) of NaBH(OAc)3 is then introduced in portions at this temperature. After leaving under stirring overnight at ambient temperature, the medium is poured into water (50 ml) and extracted twice with CH2Cl2. After drying on Na2SO4, filtration and evaporation, the residue is triturated with a 1N NaOH solution and the crystals obtained are dewatered, washed with water and then vacuum dried. 4.85 g (75%) of product is obtained.

FP=155° C.

NMR ($^1$H, CDCl$_3$): 1.43 (s; 9H, t-butyl), 1.45 (m; 2H), 1.69 (m; 2H), 1.82 (m; 2H), 1.98 (m; 2H), 3.26 (m; 2H, H1 and H5), 3.70 (s; 2H, N—CH$_2$-thioph), 3.79 (m; 1H, H3), 4.32 (m; 1H, NH-carbamate), 6.87 (m; 1H), 6.98 (m; 1H), 7.20 (m; 1H)

b) 8-(thiophen-2-ylmethyl)-8-azabicyclo[3.2.1]oct-3β-amine

This compound is obtained according to the same method as in example 8d).

NMR ($^1$H, DMSO-d$_6$): 1.28-1.34 (m; 4H), 1.47-1.57 (m; 4H), 1.85-1.89 (m; 2H), 2.78 (m; 1H, H3), 3.12 (t, J=3.0 Hz; 2H, H1 and H5), 3.67 (s; 2H, N—CH$_2$-thioph), 6.94 (m; 2H; H thioph), 7.36 (m; 1H; H thioph).

c) 3-Methylsulfanylthieno[2,3-b]pyrazine-2-carboxylic acid [8-thiophen-2-ylmethyl-8-azabicyclo[3.2.1]oct-3β-yl)amide hydrochloride This compound is prepared according to the method in example 1c), but using the corresponding reagents, i.e. 3-methylsulfanylthieno[2,3-b]pyrazine-2-carboxylic acid and the amine obtained in example 23 b).

A foam with a 29% yield is obtained.

The hydrochloride is prepared in ethyl acetate by adding isopropanol—HCl.

The hydrochloride is obtained with a 97% yield.

FP=250° C.

IR: 3425, 3235, 1642.9, 1537

NMR (base; ¹H, CDCl₃): 1.72-1.81 (m; 4H), 1.99-2.08 (m; 4H), 2.64 (s; 3H, SCH3), 3.37 (m; 2H, H1 and H5), 3.75 (s; 2H, N CH₂-thioph), 4.35-4.45 (m; 1H, H3), 6.92-6.96 (m; 2H; thioph), 7.24 (m; 1H; thioph), 8.63 (d, J=2.3 Hz; 1H; arom. H), 8.64 (d; 1H; NH), 8.76 (d, J=2.3 Hz; 1H; arom. H).

| Analysis: $C_{20}H_{22}N_4OS_3$, HCl | Mass = 467.08 |
|---|---|
| $C_{20}H_{22}N_4OS_3$, HCl, 0.26 H₂O | Mass = 477.23 |

|  | % C | % H | % N | H₂O |
|---|---|---|---|---|
| calc. | 50.34 | 5.00 | 11.74 | 0.98 |
| detect. | 50.33 | 5.00 | 11.61 | 0.96 |

MS (ESI): 431.2 (M⁺, 100%).

The invention claimed is:

1. Compounds of general formula 1

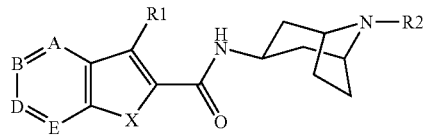

Formula 1 wherein:

A, B, D and E represent one or two nitrogen atoms, the others being carbon atoms, and X represents an S, or an O, thus forming a bicyclic merged heteroaromatic system, of the following heterocyclic systems: furo[3,2-b]pyridine, thieno[3,2-c]-pyridine, thieno[2,3-c]pyridine, thieno[3,2-b]pyridine, thieno[2,3-b]pyridine, furo[2,3-b]pyrazine or thieno[2,3-b]pyrazine, the R1 group represents a methoxy or ethoxy, and the R2 group represents a cyclohexylmethyl, a thiophene-2-ylmethyl, a thiophene-3-ylmethyl, a nonsubstituted benzyl, or a benzyl substituted by one or more F, Cl, Br, I, OMe, or CN, and their pharmaceutically acceptable salts.

2. The compounds of general formula 1, according to claim 1, wherein the A, B, D, E, X groups represent the following heterocyclic systems: furo[3,2-b]pyridine, thieno[3,2-c]pyridine, thieno[2,3-c]pyridine, thieno[3,2-b]pyridine, thieno[2,3-b]pyridine, or thieno[2,3-b]pyrazine.

3. The compounds of formula 1, according to claim 1, selected from the group consisting of:

3-Methoxythieno[2,3-b]pyridine-2-carboxylic acid (8-benzyl-8-azabicyclo[3.2.1]oct-3β-yl)amide;

3-Methoxythieno[3,2-b]pyridine-2-carboxylic acid (8-benzyl-8-azabicyclo[3.2.1]oct-3β-yl)amide;

3-Methoxyfuro[3,2-b]pyridine-2-carboxylic acid (8-benzyl-8-azabicyclo[3.2.1]oct-3β-yl)amide;

3-Methoxythieno[3,2-c]pyridine-2-carboxylic acid (8-benzyl-8-azabicyclo[3.2.1]oct-3β-yl)amide;

3-Methoxythieno[2,3-b]pyridine-2-carboxylic acid [8-(4-chlorobenzyl)-8-azabicyclo[3.2.1]oct-3β-yl]amide;

3-Methoxythieno[2,3-b]pyridine-2-carboxylic acid [8-(4-methoxybenzyl)-8-azabicyclo[3.2.1]oct-3β-yl]amide;

3-Methoxythieno[2,3-b]pyridine-2-carboxylic acid [8-(4-cyclohexylmethyl)-8-azabicyclo[3.2.1]oct-3β-yl]amide;

3-Methoxythieno[2,3-b]pyridine-2-carboxylic acid [8-(4-fluorobenzyl)-8-azabicyclo[3.2.1]oct-3β-yl]amide;

3-Methoxythieno[2,3-b]pyridine-2-carboxylic acid [8-thiophen-3-ylmethyl-8-azabicyclo[3.2.1]oct-3β-yl]amide;

3-Methoxythieno[2,3-c]pyridine-2-carboxylic acid (8-benzyl-8-azabicyclo[3.2.1]oct-3β-yl)amide;

3-Isopropoxythieno[2,3-b]pyridine-2-carboxylic acid (8-benzyl-8-azabicyclo[3.2.1]oct-3β-yl)amide;

3-Ethoxythieno[2,3-b]pyridine-2-carboxylic acid (8-benzyl-8-azabicycdo[3.2.1]oct-3β-yl)amide;

3-Methoxyfuro[3,2-b]pyridine-2-carboxylic acid 18-(4-fluorobenzyl)-8-azabicyclo[3.2.1]oct-3β-yl]amide;

3-Methoxyfuro[3,2-b]pyridine-2-carboxylic acid [8-(4-chlororobenzyl)-8-azabicyclo[3.2.1]oct-3β-yl]amide;

3-Methoxyfuro[3,2-b]pyridine-2-carboxylic acid (8-cyclchexylmethyl-8-azabicyclo[3.2.1]oct-3β-yl)amide;

3-Methylsulfanylthieno[2,3-b]pyridine-2-carboxylic acid (8-benzyl-8-azabicyclo[3.2.1]oct-3β-yl)amide;

3-Methoxythieno[2,3-b]pyrazine-2-carboxylic acid (8-benzyl-8-azabicyclo[3.2.1]oct-3β-yl)amide;

3-Methoxythieno[2,3-b]pyrazine-2-carboxylic acid [8-(4-chlorobenzyl)-8azabicyclo[3.2.1]oct-3β-yl]amide;

3-Methylsulfanylthieno[2,3-b]pyrazine-2-carboxylic acid (8-benzyl-8-azabicyclo[3.2.1]oct-3β-yl)amide;

3-Methylsulfanylthieno[2,3-b]pyrazine-2-carboxylic acid [8-(4-chlorobenzyl)-8-azabicyclo[3.2.1]oct-3β-yl]amide;

3-Methoxythieno[2,3-b]pyrazine-2-carboxylic acid [8-(4-fluorobenzyl)-8-azabicyclo[3.2.1]oct-3 13-yl)amide;

3-Methylsulfanylthieno[2,3-b]pyrazine-2-carboxylic acid [8-(4-fluorobenzyl)-8-azabicyclo[3.2.1]oct-3β-yl]amide;

3-Methoxythieno[2,3-b]pyrazine-2-carboxylic acid (8-thiophen-3-ylmethyl-8-azabicyclo[3.2.1]oct-3β-yl]amide;

3-Methoxyfuro[2,3-b]pyrazine-2-carboxylic acid (8-benzyl-8-azabicyclo[3.2.1]oct-3β-yl)amide;

3-Methoxyfuro[2,3-b]pyrazine-2-carboxylic acid [8-(4-chlorobenzyl)-8-azabicyclo[3.2.1]oct-3β-yl]amide; and 3-Methoxyfuro[2,3-b]pyrazine-2-carboxylic acid [8-(4-fluorobenzyl)-8-azabicyclo[3.2.1]oct-3β-yl]amide.

4. Method to prepare the compounds of general formula 1, according to claim 1, wherein a heterocyclic acid of formula 2,

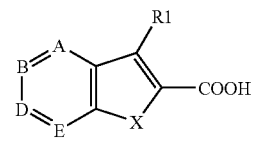

2 is allowed to react with a polycyclic amine of formula 3,

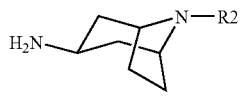

wherein the different radicals A, B, D, E, X, R1 and R2 are defined as in claim 1, under coupling conditions with the action of alkyl chloroformiate in the presence of triethylamine, in methylene chloride, at a low temperature or by the action of the acid chloride of the corresponding heterocyclic acid.

5. The compounds of formula 4, as synthesis intermediates,

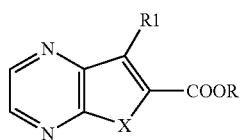

wherein X is an O or S, R1 an OH, a C1-6 alcoxy, or a C1-6 thioalcoxy, and R represents a hydrogen, except in the case where R1 is OH, R represents a methyl or an ethyl.

6. The compounds of formula 4, according to claim 5, selected from the group consisting of:

3-Hydroxy-2-methoxycarbonylfuro[2,3-b]pyrazine;
3-methylsulfanyl-2-methoxycarbonylfuro[2,3-b]pyrazine;
3-methoxy-furo[2,3-b]pyrazine-2-carboxylic acid;
3-ethoxy-furo[2,3-b]pyrazine-2-carboxylic acid;
3-methylsulfanylfuro[2,3-b]pyrazine-2-carboxylic acid;
3-Hydroxy-2-methoxycarbonylthieno[2,3-b]pyrazine;
3-methylsulfanyl-2-methoxycarbonylthieno[2,3-b]pyrazine;
3-methoxythieno[2,3-b]pyrazine-2-carboxylic acid;
3-ethoxythieno[2,3-b]pyrazine-2-carboxylic acid; and
3-methylsulfanylthieno[2,3-b]pyrazine-2-carboxylic acid.

7. A pharmaceutical formulation, comprising at least one compound of formula 1 according to claim 1, and a suitable excipient.

8. The compound according to claim 1, wherein R2 is a benzyl group optionally substituted by one or more substituents selected from the group consisting of F, Cl, Br, I, OMe or CN.

9. The pharmaceutical formulation according to claim 7, wherein said formulation is administered orally or parenterally.

10. The pharmaceutical formulation according to claim 7, wherein said formulation is administered in a dosage amount of 0.1 to 100 mg.

* * * * *